(12) United States Patent
Taillefer et al.

(10) Patent No.: US 8,604,201 B2
(45) Date of Patent: Dec. 10, 2013

(54) USE OF CYCLOVINYL PHOSPHINE/COPPER COMPLEXES AS ARYLATION CATALYSTS

(75) Inventors: Marc Taillefer, Vailhauques (FR); Hamid Kaddouri, Montpellier (FR); Fouad Ouazzani, Fes (MA)

(73) Assignee: Centre National de Recherche Scientifique (C.N.R.S.), Paris (FR)

( * ) Notice: Subject to any disclaimer, the term of this patent is extended or adjusted under 35 U.S.C. 154(b) by 767 days.

(21) Appl. No.: 12/680,607

(22) PCT Filed: Sep. 26, 2008

(86) PCT No.: PCT/FR2008/051736
§ 371 (c)(1),
(2), (4) Date: Jul. 12, 2010

(87) PCT Pub. No.: WO2009/050394
PCT Pub. Date: Apr. 23, 2009

(65) Prior Publication Data
US 2010/0298569 A1    Nov. 25, 2010

(30) Foreign Application Priority Data
Sep. 28, 2007  (FR) ..................... 07 06826

(51) Int. Cl.
*C07F 9/28* (2006.01)
*C07F 9/06* (2006.01)
(52) U.S. Cl.
USPC ............... 546/22; 546/23; 548/112; 549/218
(58) Field of Classification Search
USPC ................... 549/2, 218; 546/22, 23; 548/112
See application file for complete search history.

(56) References Cited

U.S. PATENT DOCUMENTS

2002/0058837 A1   5/2002   Suzuki et al.
2003/0236413 A1   12/2003  Cellier et al.

OTHER PUBLICATIONS

Beletskaya et al, "Copper in Cross-Coupling reactions the Post-Ullmann Chemistry", 2004, pp. 2337-2364, vol. 248, Coordination Chemistry Reviews.
Xi, Chanjuan et al, "Metallophosphination of Alkynes: Efficient Synthesis of .beta.-Functionalized Alkenylphosphines", Jan. 20, 2007, pp. 1084-1088, vol. 26, No. 4, Organometallics.
Buchwald et al, "A General and Efficient Copper Catalyst for the Amidation of Aryl Halides and the N-Arylation of Nitrogen Heterocycles", 2001, pp. 7727-7729, vol. 123, J. Am. Chem. Soc.
Ullman et al, "Over Methoxy Chlorobenzoic Acid", 1905, pp. 2120-2126, vol. 38, Ber. Dtsch. Chem. Gas (with English Abstract).
Taillefer et al, "Stereo-controlled Synthesis of Styrylphosphines and their Oxides or Sulfides Using Phosphonium Diylides", 1998, pp. 7857-7860, vol. 39, Tetrahedron Letters.
Taillefer et al, ."Reactivity of Lithium Diphenyiphosphonium Diylides Towards Phosphorus Electrophiles: Synthesis of A,B-Unsaturated Phosphorus Compounds", 2001, pp. 307-315, vo. 624, Journal of Organometallic Chemistry.

*Primary Examiner* — Andrew D Kosar
*Assistant Examiner* — Raymond Covington
(74) *Attorney, Agent, or Firm* — B. Aaron Schulman; Stites & Harbison, PLLC

(57) ABSTRACT

The invention relates to the use of cyclovinyl phosphine compounds in the form of complexes with copper, as catalysts for reactions leading to the formation of carbon-carbon and carbon-heteroatom bonds. The invention also relates to complexes of copper with at least one cyclovinyl phosphine, as well as to the method for creating a carbon-carbon or a carbon-heteroatom bond catalysed by a cyclovinyl phosphine/copper complex.

38 Claims, No Drawings

USE OF CYCLOVINYL PHOSPHINE/COPPER COMPLEXES AS ARYLATION CATALYSTS

The present invention relates to the use of cyclovinyl phosphine compounds, in the form of complexes with copper, as catalysts of carbon-heteroatom and carbon-carbon bond formation reactions.

More specifically, the present invention relates to the use of cyclovinyl phosphine/copper complex catalysts in arylation reactions of nucleophiles (nitrogen-containing, oxygen-containing, carbon-containing, and other nucleophiles), more generally in reactions leading to the creation of carbon-carbon (C—C) or carbon-heteroatom (C—HE) bonds by the Ullmann process (F. Ullmann and H. Kipper, *Ber. dtsch. Chem. Ges.*, 1905, 38, 2120-2126).

The copper-catalyzed Ullmann reaction is one of the most widely used techniques in industry, owing to the attractive cost of copper, in comparison with the costs of other noble metals such as palladium, ruthenium, and others.

The classes of molecules obtained by these reactions possess "aryl-nucleophile" (Ar-Nu) structural units which are present in a very large number of fine-chemical intermediate molecules, which are required for the preparation of active ingredients in human, animal or plant health, or even of precursors of various materials.

The industrial reactions known to date for preparing such molecules most often employ ligand/palladium catalyst systems, which are very expensive and very toxic. Such reactions, accordingly, have a low economic profitability.

There is therefore a need to provide more profitable and less toxic alternatives to the catalysts presently used in Ullmann reactions.

Recently, Buchwald et al. (*J. Am. Chem. Soc.*, 2001, 123, 7727-7729) proposed the use of conventional copper ligands for carrying out this copper-catalyzed reaction. International patent application WO-A-03/101966 describes copper ligands that allow an Ullmann reaction under mild conditions, with catalytic amounts of copper. These ligands are primarily oxime ligands, which require a specific synthesis and lead, consequently, to relatively costly reaction products.

However, the costs of catalyst systems and their toxicity may also be reduced while maintaining or even improving the yields of the above-defined coupling reactions, and while maintaining or even improving the selectivities of said reactions.

A first object of the present invention is therefore to provide compounds capable of forming complexes with copper that can be used in Ullmann reactions and lead to reaction costs lower than those incurred hitherto for such coupling reactions.

Another object is to provide compounds that are capable of forming complexes with copper and can be used in Ullmann reactions, and exhibit low toxicity and ease of synthesis, especially on an industrial scale.

As another object, the present invention aims to provide less costly catalyst systems which are of low toxicity and can be used in Ullmann coupling reactions, with high yields and high selectivities.

A further object is to provide catalyst systems which allow Ullmann coupling reactions to be carried out under mild operating conditions, especially at a temperature of less than 100° C., or even at ambient temperature, and at moderate pressure, or even at atmospheric pressure, and even in the absence of an inert reaction atmosphere.

It has now been found that the objects defined above may be obtained in entirety or in part by virtue of a catalyst system containing copper and at least one cyclovinyl phosphine compound, as described hereinbelow.

The present invention first provides the use, as a ligand of a complex comprising copper, of a cyclovinyl phosphine of formula (I):

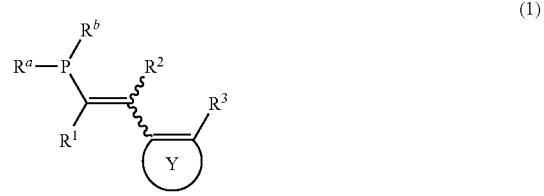

in which formula:
- $R^a$ and $R^b$, which are identical or different, preferably identical, each represent a radical independently selected from alkyl, aryl, heteroaryl, monoalkylamino, dialkylamino, alkoxy, aryloxy, heteroaryloxy, or a radical —$CR^1$=$CHR^2$—$CHR^3$=$CR^4R^5$;
- $R^1$, $R^2$ and $R^3$, which are identical or different, are selected independently from hydrogen, a hydrocarbon radical, and a heteroaryl radical; and
- the ring Y represents a mono-, bi- or tri-cyclic nucleus comprising:
  - a total of 5 to 20 members;
  - optionally one or more heteroatoms selected from nitrogen, oxygen, sulfur, and phosphorus; and
  - optionally one or more other intracyclic double bonds;
  - said cycle Y is optionally substituted by one or more chemical species selected from alkyl-G-, alkenyl-G-, alkynyl-G-, aryl-G-, heteroaryl-G- (where represents a bond, the oxygen atom or the sulfur atom), halogen, —$NO_2$, —$NH_2$, —CN, and $PR^aR^b$, where $R^a$ and $R^b$ are as defined above.

In the present invention, the following terms have the meanings hereinbelow, unless indicated otherwise:

"alkyl" or "alkyl-" represents a saturated, linear or branched, hydrocarbon radical comprising from 1 to 10 carbon atoms, preferably from 1 to 6 carbon atoms, and more particularly the methyl or ethyl radical and the propyl, butyl, pentyl, hexyl, heptyl, octyl, nonyl, and decyl radicals;

"alkenyl" or "alkenyl-" represents a hydrocarbon radical possessing at least one double bond, said radical being linear or branched and comprising from 2 to 10 carbon atoms, preferably from 2 to 6 carbon atoms, and, for example, the ethylenyl-, isopropylenyl-, or butadienyl-radical;

"alkynyl" or "alkynyl-" represents a hydrocarbon radical possessing at least one triple bond, said radical being linear or branched and comprising from 2 to 10 carbon atoms, preferably 2 to 6 carbon atoms, and, for example, the acetylenyl- or propargyl-radical;

"aryl" or "aryl-" represents a mono- or polycyclic aromatic hydrocarbon radical, and, for example, the phenyl radical or the naphthyl radical;

"heteroaryl" or "heteroaryl-" represents a mono- or polycyclic aromatic hydrocarbon radical further comprising one or more identical or different heteroatoms selected from nitrogen, oxygen, sulfur, and phosphorus, each of the rings comprising 5 or 6 members; examples of heteroaryl radicals are pyridyl, quinolyl, imidazolyl, and tetrazolyl radicals, without this list constituting any limitation;

"hydrocarbon radical" as indicated for the radicals $R^1$, $R^2$, and $R^3$ represents a branched, linear or cyclic (mono- or polycyclic) hydrocarbon radical comprising from 1 to 20 carbon atoms, which may comprise one or more unsaturations in the form of double and/or triple bond(s)—for example, and nonlimitatively, methyl, ethyl, propyl, isopropyl, butyl, isobutyl, sec-butyl, tert-butyl, cyclohexyl, benzyl, phenyl, vinyl, allyl, and the like;

in the terms "alkoxy, aryloxy, heteroaryloxy, monoalkylamino, and dialkylamino", the definitions of the terms alkyl-, aryl- and heteroaryl-correspond to the generic terms defined above;

"halogen" denotes fluorine, chlorine, brome, and iodine.

All of the radicals whose definitions feature above may optionally be substituted by one or more halogen atoms, where halogen has the aforementioned definition, by one or more alkyl, alkenyl and/or alkynyl radicals, as defined above, and/or by one or more hydroxy, alkoxy, alkenyloxy, alkynyloxy, aryl, heteroaryl, amino, alkylamino, dialkylamino, carboxy, carbonyl, carbonylamino, carbonylalkylamino and/or carbonyl-dialkylamino radicals, it being possible for the substituents to be identical or different.

The ring Y present in the phosphine of formula (1) may be a mono-, bi- or tri-cyclic, aromatic or nonaromatic nucleus which optionally carries one or more heteroatoms selected from nitrogen, oxygen, sulfur, and phosphorus.

The monocyclic nuclei include, as nonlimitative examples, cyclopentene, cyclopentadiene, pyrroles, imidazoles, pyrrolines, imidazolines, pyrazolines, furan, dihydrofuran, thiophene, dihydrothiophene, isoxazoles, thiazoles, and isothiazoles, and also their dihydrogenated analogs, benzene, cyclohexadienes, cyclohexene, pyridine and its di- and tetrahydrogenated analogs, pyrazines, pyrimidines, and pyridazines, and their di- and tetra-hydrogenated analogs, pyrans and dihydropyrans, triazine and its di- and tetra-hydrogenated analogs, dithiazine, cycloheptene, cycloheptadienes, azepines and their partially hydrogenated analogs, cyclooctene, cyclooctadienes, cyclooctatriene, and azocines, and their partially hydrogenated analogs.

In one preferred embodiment the ring present in the phosphine of formula (1) is a substituted or unsubstituted pyridine ring.

Bicyclic nuclei include, as nonlimitative examples, pentalene, indane, indenes, bornenes, norbornenes, naphthalene, azulene, heptalene, cyclopentacyclooctene, benzocycloheptenes, benzocyclooctene, indolizine, indole, isoindole, quinazolines, quinoline, isoquinoline, phthalazine, naphthyridine, quinoxaline, cinnoline, chromans, isochromans, chromenes, and isochromenes, indolines and isoindolines, and the partially hydrogenated analogs of each of these compounds.

Tricyclic nuclei include, as nonlimitative examples, indacenes, acenaphthylenes, fluorene, phenalene, phenanthrene, anthracene, thianthrene, xanthene, phenoxathiine, carbazoles, carboline, phenanthridine, acridine, perimidine, phenanthroline, phenazine, phenothiazine, phenoxazine, and the partially hydrogenated analogs of each of these compounds.

In the preceding paragraphs, the term "partially hydrogenated analogs" indicates analogs in which there remains at least one double bond between two carbon atoms, these two carbon atoms not being both at the junction of two or three nuclei.

In the structural formula of the compound of formula (1) as indicated earlier on above, the bonds in "wiggly" lines indicate that the two double bonds may each be located in cis or trans configuration, in other words that the cyclovinyl phosphine of formula (1) may be of E or Z configuration.

With regard to the double bond connected to the phosphorus atom, the cyclovinyl phosphines obtained by the method of the invention may be specifically of Z configuration (formula (1Z)) or of E configuration (formula (1E)), or in the form of a mixture in any proportions:

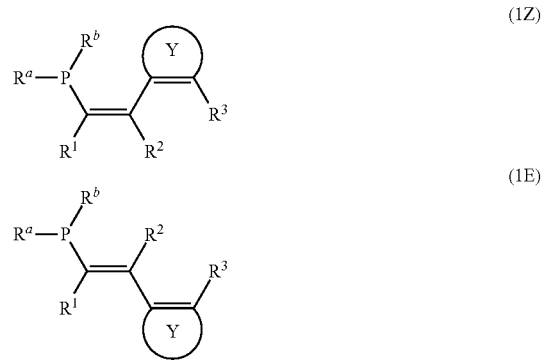

The E and Z isomers of the phosphines obtained by the method of the present invention may be separated, if necessary, by methods or techniques which are conventional and are known to a person skilled in the art.

According to the intended applications, preference is given to cyclovinyl phosphines of formula 1Z, or cyclovinyl phosphines of formula 1E, or else mixtures of cyclovinyl phosphines 1E and 1Z, in any proportions.

According to one aspect of the invention, preference is given to compounds of formula (1) which possess the following characteristics, taken in isolation or in combination of two or more thereof:

$R^a$ and $R^b$, which are identical or different, each represent a radical independently selected from alkyl, especially methyl, ethyl, propyl or butyl, aryl, especially phenyl or naphthyl, heteroaryl, especially pyridyl or quinolyl, and preferably $R^a$ and $R^b$ are identical and each represent phenyl;

$R^1$ represents hydrogen or alkyl, especially methyl, ethyl or propyl, and preferably $R^1$ represents hydrogen;

$R^2$ and $R^3$, which are identical or different, are selected independently from hydrogen, an alkyl radical, an aryl radical, and a heteroaryl radical, more particularly from hydrogen and an alkyl radical, especially methyl, ethyl or propyl; and Y represents a mono-, bi- or tri-cyclic nucleus, preferably a monocyclic nucleus comprising 5 or 6 members and optionally 1, 2 or 3 heteroatoms selected from nitrogen, oxygen, and sulfur, Y being preferably an aromatic nucleus which is optionally substituted by one or more chemical species selected from alkyl-G-, alkenyl-G-, alkynyl-G-, aryl-G-, heteroaryl-G- (where G represents a bond, the oxygen atom or the sulfur atom), halogen, $-NO_2$, $-NH_2$, $-CN$, and $PR^aR^b$, where $R^a$ and $R^b$ are as defined above.

According to another aspect of the invention, preference is given to the compounds of formula (1) which possess the following characteristics:

$R^a$ and $R^b$, which are identical or different, each represent a radical independently selected from aryl, especially phenyl or naphthyl, and heteroaryl, especially pyridyl or quinolyl, and preferably $R^a$ and $R^b$ are identical and each represent phenyl;

$R^1$, $R^2$, and $R^3$, which are identical or different, are selected independently from hydrogen and an alkyl radical, especially methyl, ethyl or propyl; and Y represents a monocyclic nucleus, preferably a monocyclic nucleus comprising 6 members and optionally 1, 2 or 3 heteroatoms, preferably 1 heteroatom, selected from nitrogen, oxygen, and sulfur, preferably nitrogen, Y being preferably an aromatic nucleus which is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —$NO_2$, —$NH_2$, —CN, and $PR^aR^b$, where $R^a$ and $R^b$ are as defined above.

Very preferably, the use as claimed in the present invention employs a compound of formula (1) in which:

$R^a$ and $R^b$ are identical and each represent a phenyl radical;
$R^1$, $R^2$, and $R^3$ are identical and each represent the hydrogen atom; and
the ring Y represents a benzene or pyridine nucleus, the nitrogen atom of the pyridine nucleus being advantageously in α position relative to the double bond present in the formula (1), Y being optionally substituted, but preferably not substituted, by one or more chemical species selected from alkyl-G-, alkenyl-G-, alkynyl-G-, aryl-G-, heteroaryl-G- (where G represents a bond, the oxygen atom or the sulfur atom), halogen, —$NO_2$, —$NH_2$, and —CN.

The compounds of formula (1) defined above may be obtained from compounds which are readily available commercially, or may be easily prepared on the basis of procedures which are known in the literature, for example, as described by M. Taillefer and H. J. Cristau, *Tet. Lett.*, 39, (1998), 7857, or else M. Taillefer et al., *J. Organometall. Chem.*, 624, (2001), 307-315.

For example, the method of preparing the compounds of formula (1) may advantageously be carried out in a single operation ("one pot"), in other words without any need to isolate and/or purify the synthesis intermediates. It is possible, though, to isolate and/or purify the intermediates, for the purpose, for example, of studying the effective progress of the reaction or its kinetics, or of analyzing the intermediates formed, and others.

Accordingly, an example of a process for preparing the compounds of formula (1) comprises the steps of:

a) contacting a phosphonium halide of formula (2) with a strong base in an aprotic polar solvent, tetrahydrofuran for example, at low temperature, generally between −70° C. and 0° C., −50° C. for example, to give the phosphonium diylide (3):

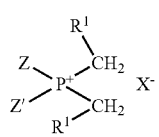

(2)

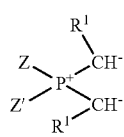

(3)

where $R^1$ is as defined above, Z and Z' possess definitions which are identical to those of $R^a$ and $R^b$ defined above, and X represents a halogen atom selected from fluorine, chlorine, bromine, and iodine;

b) the diylide (3) is reacted in an aprotic polar solvent medium, tetrahydrofuran for example, at a temperature generally of between −70° C. and +10° C., −10° C. for example, with a halophosphine (4):

(4)

where $R^a$ and $R^b$ are as defined above and X' represents a halogen atom selected from fluorine, chlorine, bromine, and iodine;

to give the phosphonium ylide (5a), which undergoes prototropic rearrangement to give the phosphonium ylide (5b):

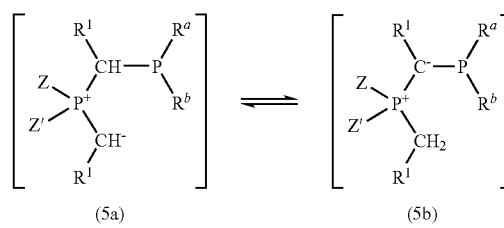

(5a)     (5b)

where $R^a$, $R^b$, $R^1$, Z, and Z' are as defined above;

c) the ylide (5b) then being contacted, generally at a temperature of between 0° C. and 50° C., at ambient temperature for example, in an aprotic polar solvent, such as tetrahydrofuran, with an α,β-unsaturated, carbonyl-containing cyclic derivative of formula (6):

(6)

in which $R^2$, $R^3$ and Y are as defined above, to give, following removal of the solvent and optional purification, the cyclovinyl phosphine of formula (1).

The method described above may advantageously be carried out in a single reactor ("one pot"), which means that there is no need to isolate some or all of the intermediates. It is possible, however, of course and if desired, to isolate one or more of the intermediates, advantageously when they are stable.

The strong base used for preparing the phosphonium diylide (3) described above is generally a metallic base, by which is meant a strong base comprising one or more metals, advantageously selected from alkali metals and alkaline earth metals, and more particularly from lithium, sodium, potassium, magnesium, calcium, and barium. Strong lithiated bases are preferred, especially butyllithium. In that case the counterion of the phosphonium diylide (3) is the lithium cation.

According to the present invention, the cyclovinyl phosphines of formula (1) are used as ligands for copper to form complexes.

This is because the cyclovinyl phosphines are of great interest in coordination chemistry and in catalysis, owing to the fact that they combine two ligands which are very important in organometallic chemistry: two (or more) conjugated double bonds, and the phosphorus atom of the phosphine group. The above-described cyclovinyl phosphines may further comprise other coordination sites, more particularly when they comprise radicals or nuclei which carry heteroatoms that are capable of forming coordinative bonds.

Complexes of this kind, of copper with at least one cyclovinyl phosphine of formula (1) as defined above, constitute a further subject of the present invention.

The complexes according to the invention may be represented schematically in the form Pho-CyV/Cu, where Pho-CyV represents a cyclovinyl phosphine of formula (1) defined above, and Cu represents a copper atom. This schematic representation does not in any way indicate the number of moles of cyclovinyl phosphine that are present in relation to the number of atoms of copper that are present.

A "monomeric complex" is a Pho-CyV/Cu complex which comprises one copper atom, a "dimeric complex" is a Pho-CyV/Cu complex which comprises two copper atoms, a "trimeric complex" is a Pho-CyV/Cu complex which comprises three copper atoms, etc.

Examples of complexes according to the invention include the dimeric pyridylvinyldiphenylphosphine/-copper iodide complex $[C_5H_4N—CH=CH—PPh_2]_2Cu_2I_2$, where Ph represents the phenyl radical, in the form of the Z or E isomer, pure or as a mixture of said two isomers in any proportions.

The Pho-CyV/Cu complexes defined above may be prepared by conventional procedures that are known to a person skilled in the art. For example, the Pho-CyV/Cu complexes may be prepared by contacting at least one cyclovinyl phosphine, especially of formula (1) defined above, with metallic copper or a copper derivative (copper(I) or copper(II)), for example, a copper halide, such as cupric or cuprous iodide, bromide or chloride, or other derivatives, especially organocopper compounds, for example, copper acetylacetonate.

The reaction is generally performed under an inert atmosphere, as for example under nitrogen or argon, in an organic solvent medium, preferably an aprotic polar solvent, for example, acetonitrile. The complexing reaction is commonly conducted at a temperature of between 0° C. and 80° C., depending on the nature of the compounds present, and generally the reaction temperature is the ambient temperature.

The complex is generally obtained in the form of a precipitate, which is isolated from the reaction mixture by procedures which are known per se, as for example by filtration, and optionally recrystallization from a solvent, which advantageously is identical with that used for the complexing reaction.

According to one variant, the Pho-CyV/Cu complex may be advantageously prepared in situ in the reaction mixture of the reaction which is catalyzed by the Pho-CyV/Cu complex.

The present invention thus relates to the use, as a ligand of a complex comprising copper, of a cyclovinyl phosphine of formula (1) as described above. The cyclovinyl phosphine/copper complex (referred to as Pho-CyV/Cu in the remainder of the present specification) may itself be used in a large number of catalytic reactions, more particularly reactions employing a copper-based catalyst, and more particularly, and advantageously, catalytic coupling reactions, known as Ullmann reactions.

Thus, according to another aspect, the present invention provides a method of creating a carbon-carbon (C—C) bond or carbon-heteroatom (C—HE) bond by reacting a compound which carries a leaving group with a nucleophilic compound which carries a carbon atom or a heteroatom (HE) which can be capable of replacing the leaving group, thereby creating a C—C or C—HE bond, in which method the reaction is carried out in the presence of an effective amount of a catalyst system comprising at least one cyclovinyl phosphine/copper complex.

The inventors have now found that catalyst systems based on copper complexed with a cyclovinyl phosphine allow the creation of a carbon-carbon (C—C) bond or of a carbon-heteroatom (C—HE) bond by reaction of a compound which carries a leaving group with a nucleophilic compound which carries a carbon atom or a heteroatom (HE) capable of replacing the leaving group, thereby creating a C—C or C—HE bond.

The general scheme of the method according to the present invention may be illustrated as follows:

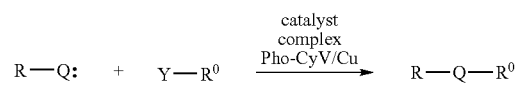

in which:
- Y—$R^0$ represents a compound which carries a leaving group Y; and
- R-Q: represents a nucleophilic compound, R being the residue of said nucleophilic compound and Q being a carbon atom or a heteroatom (HE) which is capable of replacing said leaving group Y.

According to a first variant of the method of the present invention, an arylation reaction is carried out by reacting an aromatic compound which carries a leaving group with a nucleophilic compound.

According to another variant of the method of the invention, a vinylation or alkynation reaction is carried out by reacting, respectively, a compound comprising a double bond or a triple bond in a position to a leaving group, with a nucleophilic compound.

In the description below of the present invention, the term "arylation" is used in its broad sense, since the intended use is of an unsaturated compound which carries a leaving group which is alternatively of unsaturated aliphatic or of carbocyclic or heterocyclic aromatic type.

A "nucleophilic compound" means an organic hydrocarbon compound, alternatively acyclic or cyclic or polycyclic, which has the characteristic of comprising at least one atom which carries a lone pair, which may or may not comprise a charge, and preferably a nitrogen, oxygen, sulfur, boron or phosphorus atom, or comprises a carbon atom which is able to donate its pair of electrons.

As mentioned above, the nucleophilic compound comprises at least one atom which carries a lone pair, which may be provided by a functional group and/or a carbanion.

Functional groups and/or carbanions which comprise said at least one atom include especially the following atoms and groups:

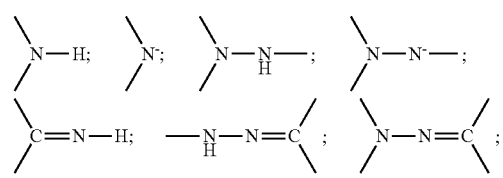

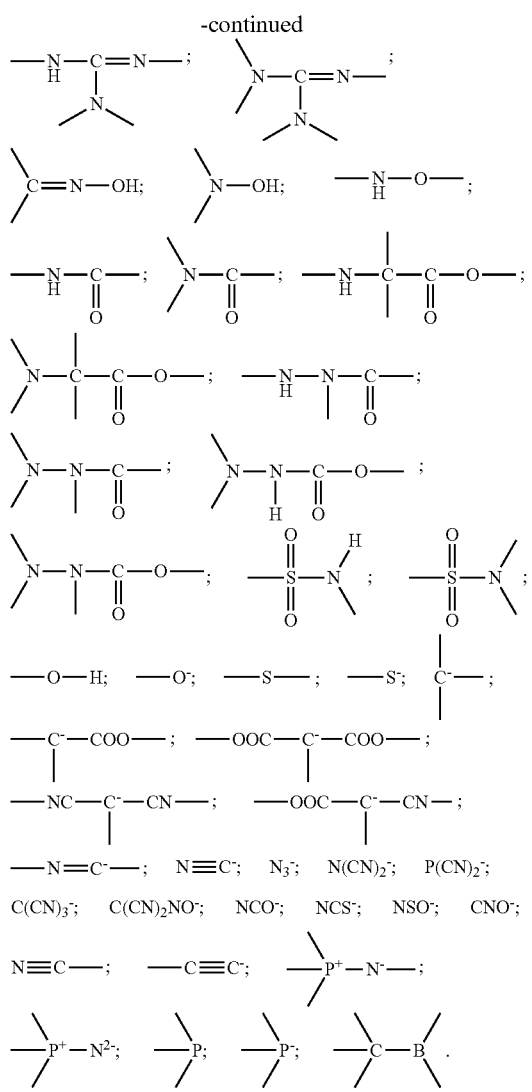

According to another variant of the invention, the nucleophilic compound comprises at least one nitrogen atom which carries a lone pair, and is part of a saturated, unsaturated or aromatic ring; the ring generally comprises from 3 to 8 atoms.

It should be noted that when the nucleophilic compound comprises a functional group, examples of which are given above, and said group carries one or more negative charges, said compound is in that case in a salified form. The counterion is generally a metal cation, such as an alkali metal, preferably lithium, sodium or potassium, or an alkaline earth metal, preferably calcium, or the residue of an organometallic compound, such as especially an organomagnesium or organozinc compound.

A first advantage of the method of the invention is of performing the reaction at moderate temperature.

Another advantage is to be able to use a wide range of coupling agents, more particularly arylating agents, nucleophiles, not only iodides but also bromides, chlorides or triflates, especially aryl iodides, aryl bromides, aryl chlorides or aryl triflates.

A further advantage of the method of the invention is of employing catalysis by copper rather than palladium or nickel, in other words a catalyst which is less toxic and further provides an advantage from the economic standpoint.

The method of the invention is of interest in respect of a large number of nucleophilic compounds, and examples are given below, for illustration, without any limitative character whatsoever.

A first category of substrates (nucleophilic compounds) to which the method of the invention applies comprises nitrogen-containing organic derivatives, and more particularly primary or secondary amines; hydrazine or hydrazone derivatives; amides; sulfonamides; urea derivatives; and heterocyclic derivatives, preferably nitrogen-containing and/or sulfur-containing heterocyclic derivatives.

More specifically the primary or secondary amines may be represented by the general formula (Ia):

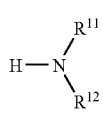

(Ia)

in which formula (Ia):

$R^{11}$ and $R^{12}$, which are identical or different, are selected from hydrogen, a hydrocarbon radical (1 to 20 carbon atoms, as defined above), an aryl radical, a heteroaryl radical, and from any concatenation of two or more of the aforementioned groups, with the proviso that not more than one of the groups $R^{11}$ and $R^{12}$ represents the hydrogen atom.

The amines employed with preference are of the formula (Ia) in which $R^{11}$ and $R^{12}$, which are identical or different, represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $O_{12}$ aryl or arylalkyl group.

More particular examples of groups $R^{11}$ and $R^{12}$ include $C_1$ to $C_4$ alkyl, phenyl, naphthyl or benzyl groups.

More specific examples of amines of formula (Ia) include aniline, N-methylaniline, diphenylamine, benzylamine, and dibenzylamine.

The present invention does not exclude the presence of one or more unsaturations in the hydrocarbon chain or chains, such as one or more double and/or triple bonds, which may be conjugated or nonconjugated.

The hydrocarbon chain or chains may also be interrupted by one or more heteroatoms (for example, oxygen, sulfur, nitrogen, phosphorus), and/or by a nonreactive functional group, such as —CO—, for example.

It should be noted that the amino group can be in the form of anions. The counterion is then a metal cation, preferably an alkali metal cation and more preferably sodium or potassium. Mention may be made, as examples of such compounds, of sodium amide or potassium amide.

The hydrocarbon chain can optionally carry one or more substituents, as indicated above, in particular atoms, groups or radicals selected from halogen, ester, amino, alkylphosphine and/or arylphosphine, insofar as they do not interfere.

The saturated or unsaturated and linear or branched acyclic aliphatic groups can optionally carry a cyclic substituent. The term "ring" denotes a saturated, unsaturated or aromatic carbocyclic or heterocyclic ring.

The acyclic aliphatic group can be connected to the ring via a valence bond, a heteroatom or a functional group, such as oxy, carbonyl, carboxyl, sulfonyl, and the like.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents themselves optionally carrying any substituent, insofar as they do not interfere with the reactions occurring in the process of the invention. Mention may in particular be made of the alkyl or alkoxy groups comprising from 1 to 4 carbon atoms.

Among the aliphatic groups carrying a cyclic substituent, cycloalkylalkyl groups, for example cyclohexylalkyl groups, or arylalkyl groups, preferably $C_7$ to $C_{12}$, in particular benzyl or phenylethyl groups, are more particularly targeted.

In the general formula (Ia), the $R^{11}$ and $R^{12}$ groups can also represent, independently of one another, a saturated carbocyclic group or a carbocyclic group comprising one or two unsaturations in the ring, generally a $C_3$ to $C_8$ ring, preferably comprising 6 carbon atoms in the ring; it being possible for said ring to be substituted. Mention may be made, as preferred examples of groups of this type, of cyclohexyl groups which are optionally substituted, in particular by linear or branched alkyl groups having from 1 to 4 carbon atoms.

The $R^{11}$ and $R^{12}$ groups can represent, independently of one another, an aromatic hydrocarbon group and in particular a benzene hydrocarbon group corresponding to the general formula ($F_1$):

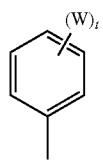

(F₁)

in which:
t represents 0, 1, 2, 3, 4 or 5; and
W represents a group chosen from linear or branched $C_1$-$C_6$ alkyl, linear or branched $C_1$-$C_6$ alkoxy, linear or branched $C_1$-$C_6$ alkylthio, —$NO_2$, —CN, halogen and $CF_3$.

The aromatic hydrocarbon group can thus be substituted. W illustrates some types of preferred substituents but the list is not limiting.

$R^{11}$ and $R^{12}$ can also represent, independently of one another, a polycyclic aromatic hydrocarbon group with the rings being able to form, with one another, ortho-fused or ortho- and peri-fused systems. Mention may more particularly be made of a naphthyl group, it being possible for said ring to be substituted.

$R^{11}$ and $R^{12}$ can also represent, independently of one another, a polycyclic hydrocarbon group composed of at least two saturated and/or unsaturated carbocycles or of at least two carbocycles, only one of which is aromatic, which form, with one another, ortho- or ortho- and peri-fused systems. Generally, the rings are $C_3$ to $C_8$ rings, preferably $C_6$ rings. Mention may be made, as more specific examples, of the bornyl group or the tetrahydronaphthalene group.

$R^{11}$ and $R^{12}$ can also represent, independently of one another, a saturated, unsaturated or aromatic heterocyclic group comprising in particular 5 or 6 atoms in the ring, including one or two heteroatoms, such as nitrogen atoms (unsubstituted by a hydrogen atom), sulfur atoms and oxygen atoms; it being possible for the carbon atoms of this heterocycle also to be substituted.

$R^{11}$ and $R^{12}$ can also represent a polycyclic heterocyclic group defined as being either a group composed of at least two aromatic or nonaromatic heterocycles comprising at least one heteroatom in each ring and forming, with one another, ortho- or ortho- and peri-fused systems or a group composed of at least one aromatic or nonaromatic hydrocarbon ring and at least one aromatic or nonaromatic heterocycle forming, with one another, ortho- or ortho- and peri-fused systems, it being possible for the carbon atoms of said rings optionally to be substituted.

Mention may be made, as examples of $R^{11}$ and $R^{12}$ groups of heterocyclic type, inter alia, of the furyl, thienyl, isoxazolyl, furazanyl, isothiazolyl, pyridyl, pyridazinyl, pyrimidinyl, pyranyl or phosphino groups and the quinolyl, naphthyridinyl, benzopyranyl or benzofuranyl groups.

The number of substituents present in each ring depends on the carbon fusion of the ring and on the presence or absence of unsaturation in the ring. The maximum number of substituents capable of being carried by a ring is easily determined by a person skilled in the art.

Other nucleophilic compounds capable of being employed in the process of the invention are, for example, the hydrazine derivatives corresponding to the formula (Ib):

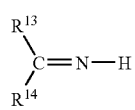

(Ib)

in which:
$R^{13}$ and $R^{14}$, which are identical or different, have the meanings given for $R^{11}$ and $R^{12}$ in the formula (Ia) and at most one of the $R^3$ and $R^4$ groups represents a hydrogen atom.

The $R^{13}$ and $R^{14}$ groups more particularly represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group. More preferably, $R^{13}$ and $R^{14}$ represent a $C_1$ to $C_4$ alkyl, phenyl, benzyl or naphthyl group.

Mention may be made, as other nucleophiles, of oximes and hydroxylamines, which can be represented by the general formulae (Ic) and (Id) respectively:

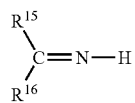

(Ic)

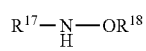

(Id)

in which formulae:
$R^{15}$ and $R^{16}$, which are identical or different, have the definitions given for $R^{11}$ and $R^{12}$ in the formula (Ia) and at most one of the $R^{15}$ and $R^{16}$ groups represents a hydrogen atom;
$R^{17}$ has the definitions given for $R^{11}$ or $R^{12}$ in the formula (Ia), with the exception of the hydrogen atom; and
$R^{18}$ is chosen from the hydrogen atom, a saturated or unsaturated and linear or branched acyclic aliphatic group and a saturated or unsaturated monocyclic or polycyclic carbocyclic group, and from any sequence of two or more of said groups.

Preferred examples of oximes or hydroxylamines of formulae (Ic) and (Id) respectively are those for which $R^{15}$, $R^{16}$ and $R^{17}$ represent $C_1$ to $C_{15}$, preferably $C_1$ to $C_{10}$, alkyl, $C_3$ to $C_8$, preferably $C_5$ or $C_6$, cycloalkyl or $C_6$ to $C_{12}$ aryl or arylalkyl.

Mention may be made, as more particular examples of $R^{15}$, $R^{16}$ and $R^{17}$ groups, of $C_1$ to $C_4$ alkyl, phenyl, naphthyl or benzyl groups. With regard to $R^{18}$, it preferably represents $C_1$ to $C_4$ alkyl or benzyl.

According to another aspect, the present invention employs nucleophilic compounds of hydrazine type which can be represented by the following formula (Ie):

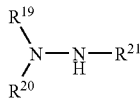
(Ie)

in which:
$R^{19}$, $R^{20}$ and $R^{21}$, which are identical or different, have the definitions given for $R^{11}$ and $R^{12}$ in the formula (Ia);
$R^{21}$ represents a hydrogen atom or a protective group G; and
at least one of the $R^{19}$, $R^{20}$ and $R^{21}$ groups does not represent a hydrogen atom;
or else $R^{19}$ and $R^{20}$ can together form, with the nitrogen atom which carries them, a saturated, unsaturated or aromatic monocyclic or polycyclic $C_3$-$C_{20}$ heterocyclic group.

Preferred hydrazines of formula (Ie) above are those in which $R^{19}$ and $R^{20}$, which are identical or different, represent $C_1$-$C_{15}$, preferably $C_1$-$C_{10}$ alkyl, $C_3$-$C_8$, preferably $C_5$ or $C_6$, cycloalkyl or $C_6$-$C_{12}$ aryl or arylalkyl. More preferably, the hydrazines are those of formula (Ie) in which $R^{11}$ and $R^{20}$, which are identical or different, represent $C_1$ to $C_4$ alkyl, phenyl, benzyl or naphthyl.

$R^{19}$ and $R^{20}$ can be connected together, so as to form, with the nitrogen atom which carries them, a saturated, unsaturated or aromatic monocyclic or polycyclic $C_3$-$C_{20}$ heterocyclic group comprising two or three ortho-fused rings, that is to say at least two rings which have two carbon atoms in common.

For the polycyclic compounds, the number of atoms of each ring can preferably vary between 3 and 6. According to a preferred embodiment, $R^{19}$ and $R^{20}$ together form a cyclohexane or fluorenone ring.

In the above formula (Ie), $R^{21}$ preferably represents a hydrogen atom, alkyl (preferably $C_1$-$C_{12}$), alkenyl or alkynyl (preferably $C_2$-$C_{12}$), cycloalkyl (preferably $C_3$-$C_{12}$), or aryl or arylalkyl (preferably $C_6$-$C_{12}$). More preferably, $R^{21}$ represents a hydrogen atom or a $C_1$-$C_4$ alkyl group.

It should be noted that, when the nucleophilic compound comprises an $NH_2$ group, both hydrogen atoms can react. In such a case, and in order to increase the selectivity of the reaction, one or both hydrogen atoms can advantageously be masked by the use of a protective group. Such protective groups are well known in the field and mention may be made of the protective groups commonly used, such as, for example, acyl (acetyl, benzoyl), BOC (butoxycarbonyl), CBZ (carbobenzoxy), FMOC (trifluoromethyloxycarbonyl) or MSOC (2-(methane-sulfenyl)ethoxycarbonyl) groups. Reference may be made, on this subject, for example, to the work by T. W. Greene et al., *Protective Groups in Organic Synthesis*, 2$^{nd}$ edition, John Wiley & Sons Inc., as regards the reactions for protecting and deprotecting amino groups.

Other nucleophilic compounds which can be employed in the process of the present invention are the compounds of hydrazone type, which can be represented by the formula (If):

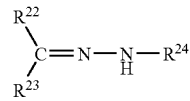
(If)

in which:
$R^{22}$, $R^{23}$ and $R^{24}$, which are identical or different, have the definitions given for $R^{11}$ and $R^{12}$ in the formula (Ia);
at most one of the $R^{22}$ and $R^{23}$ groups represents the hydrogen atom;
or else $R^{22}$ and $R^{23}$ can together form, with the nitrogen atom which carries them, a saturated, unsaturated or aromatic, monocyclic or polycyclic $C_3$-$C_{20}$ carbocyclic or heterocyclic group.

Preferred examples of hydrazones of above formula (If) are those in which $R^{22}$ and $R^{23}$, which are identical or different, represent $C_1$-$C_{15}$, preferably $C_1$-$C_{10}$, alkyl, $C_3$-$C_8$, preferably $C_5$ or $C_6$, cycloalkyl, or $C_6$-$C_{12}$ aryl or arylalkyl. More preferably, examples of hydrazones of formula (If) are those in which $R^{22}$ and $R^{23}$, which are identical or different, represent $C_1$ to $C_4$ alkyl, phenyl, benzyl or naphthyl.

$R^{22}$ and $R^{23}$ can together form, with the nitrogen atom which carries them, a saturated, unsaturated or aromatic, monocyclic or polycyclic $C_3$-$C_{20}$ carbocyclic or heterocyclic group comprising two or three ortho-fused rings.

For the polycyclic compounds, the number of atoms of each ring can preferably vary between 3 and 6. According to a preferred embodiment, $R^{22}$ and $R^{23}$ together form a cyclohexane or fluorenone ring.

In the above formula (If), $R^{24}$ preferably represents a hydrogen atom or an alkyl group (preferably $C_1$-$C_{12}$), alkenyl or alkynyl (preferably $C_2$-$C_{12}$), cycloalkyl (preferably $C_3$-$C_{12}$), or aryl or arylalkyl (preferably $C_6$-$C_{12}$) group. More preferably, $R^{24}$ represents a hydrogen atom or a $C_1$-$C_4$ alkyl group.

The invention is also targeted at the compounds of amide type corresponding more particularly to the formula (Ig):

in which $R^{25}$ and $R^{26}$ have the meanings given for $R^{11}$ and $R^{12}$ in the formula (Ia).

Mention may be made, as examples of compounds of formula (Ig), of oxazolidin-2-one, benzamide and acetamide.

The invention also applies to compounds of sulfonamide type which can, for example, correspond to the formula (Ih):

in which $R^{27}$ and $R^{28}$ have the meanings given for $R^{11}$ and $R^{12}$ in the formula (Ia).

Mention may be made, as example of compounds of formula (Ih), of tosylhydrazide.

Mention may be made, as other types of nucleophilic substrates, of urea derivatives, such as guanidines, which can be represented by the formula (Ii):

(Ii)

in said formula (Ii), the $R^{29}$ groups, which are identical or different, have the meanings given for $R^{11}$ and $R^{12}$ in the formula (Ia).

Mention may be made, as example of compounds of formula (Ii), of N,N,N',N'-tetramethylguanidine.

Yet other examples of nucleophilic compounds which can be used in the process of the present invention comprise amino acids and their derivatives, for example those corresponding to the following formula (Ij):

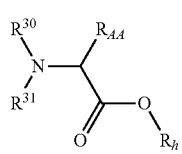

(Ij)

in which:
- $R_{AA}$ represents a hydrogen atom or the residue of an amino acid, preferably a hydrogen atom; a linear or branched $C_1$-$C_{12}$ alkyl optionally carrying a functional group; a $C_6$-$C_{12}$ aryl or arylalkyl; or a functional group, preferably a hydroxyl group;
- $R^{30}$ and $R^{31}$ have the definitions given for $R^{11}$ and $R^{12}$ in the formula (Ia);
- $R_h$ represents a hydrogen atom, a metal cation, preferably an alkali metal cation, or a $C_1$-$C_{12}$ hydrocarbon group, preferably a $C_1$-$C_{12}$ alkyl group.

According to a preferred embodiment, $R_{AA}$ in the above formula (Ij) represents alkyl, optionally comprising a functional group, for example —OH, —NH$_2$, —CO—NH$_2$, —NH—CNH—, —HN—C(O)—NH$_2$, —COOH, —SH or —S—CH$_3$, or an imidazole, pyrrole or pyrazole group.

Examples of such amino acids comprise glycine, cysteine, aspartic acid, glutamic acid or histidine.

Nucleophilic substrates entirely well suited to the use of the process of the invention are the heterocyclic derivatives comprising at least one nucleophilic atom, such as a nitrogen, sulfur or phosphorus atom.

More specifically, such compounds correspond to the general formula (Ik):

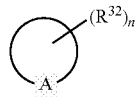

(Ik)

in said formula (Ik):
- A symbolizes the residue of a ring forming all or part of an aromatic or nonaromatic and monocyclic or polycyclic heterocyclic system, one of the carbon atoms of which is replaced by at least one nucleophilic atom, such as a nitrogen, sulfur or phosphorus atom;
- $R^{32}$, which is (are) identical or different, represent(s) the substituent(s) of the ring;
- n represents the number of substituents on the ring.

The invention applies in particular to the monocyclic heterocyclic compounds corresponding to the formula (Ik) in which A symbolizes a saturated, unsaturated or aromatic heterocycle comprising in particular 5 or 6 atoms in the ring which can comprise from 1 or 3 heteroatoms, such as nitrogen, sulfur and oxygen atoms, from among which at least one is a nucleophilic atom, such as NH or S.

A can also represent a polycyclic heterocyclic compound defined as being composed of at least two aromatic or nonaromatic heterocycles comprising at least one heteroatom in each ring and forming, with one another, ortho- or ortho- and peri-fused systems or a group composed of at least one aromatic or nonaromatic carbocycle and at least one aromatic or nonaromatic heterocycle forming, with one another, ortho- or ortho- and peri-fused systems.

It is also possible to start from a substrate resulting from the linking of a saturated, unsaturated or aromatic heterocycle, such as Mentioned above, and of a saturated, unsaturated or aromatic carbocycle. Carbocycle is preferably understood to mean a ring of cycloaliphatic or aromatic type having from 3 to 8 carbon atoms, preferably 6 carbon atoms.

It should be noted that the carbon atoms of the heterocycle can optionally be substituted, in their entirety or for a portion of them only, by $R^{32}$ groups.

The number of substituents present on the ring depends on the number of atoms in the ring and on the presence or absence of unsaturations in the ring. The maximum number of substituents capable of being carried by a ring is easily determined by a person skilled in the art.

In the formula (Ik), n is preferably 0, 1, 2, 3 or 4; more preferably, n is equal to 0 or 1.

Examples of substituents are given below but this list does not exhibit a limiting nature.

The $R^{32}$ group or groups, which are identical or different, preferably represent one of the following groups:
- a linear or branched $C_1$ to $C_6$, preferably $C_1$ to $C_4$, alkyl group, such as methyl, ethyl, propyl, isopropyl, butyl, isobutyl, sec-butyl or tert-butyl;
- a linear or branched $C_2$ to $C_6$, preferably $C_2$ to $C_4$, alkenyl or alkynyl group, such as vinyl or allyl;
- a linear or branched $C_1$ to $C_6$, preferably $C_1$ to $C_4$, alkoxy or thioether group, such as the methoxy, ethoxy, propoxy, isopropoxy or butoxy groups, an alkenyloxy group, preferably an allyloxy group, or a phenoxy group;
- a cyclohexyl, phenyl or benzyl group;
- a group or a functional group, such as hydroxyl, thiol, carboxyl, ester, amide, formyl, acyl, aroyl, amide, urea, isocyanate, thioisocyanate, nitrile, azide, nitro, sulfone, sulfo, halogen, pseudohalogen or trifluoromethyl.

The present invention applies very particularly to the compounds corresponding to the formula (Ik) in which the $R^{32}$ group or groups more particularly represent an alkyl or alkoxy group.

More particularly, the optionally substituted residue A represents one of the following rings:
- a monocyclic heterocycle comprising one or more heteroatoms:

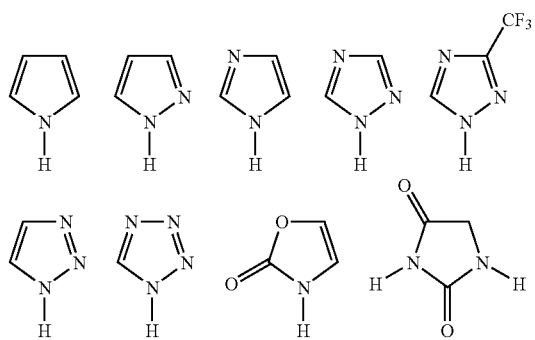

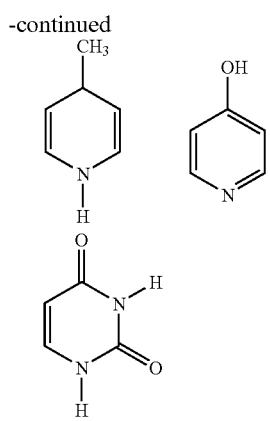

a bicycle comprising a carbocycle and a heterocycle comprising one or more heteroatoms:

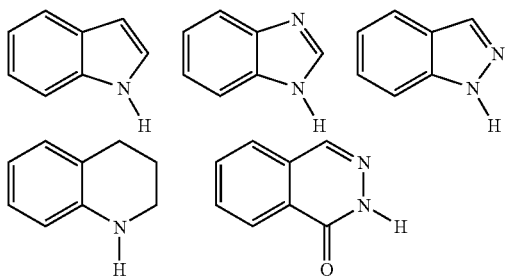

a tricycle comprising at least one carbocycle or one heterocycle comprising one or more heteroatoms:

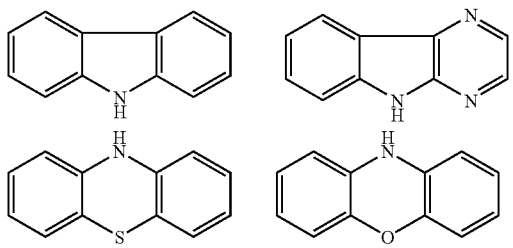

As examples of heterocyclic compounds, it is preferable to use those which correspond to the formula (Ik) in which A represents a ring such as imidazole, pyrazole, triazole, pyrazine, oxadiazole, oxazole, tetrazole, indole, pyrrole, phthalazine, pyridazine or oxazolidine.

As regards the nucleophilic compounds capable of also being employed in the process of the invention, mention may also be made of the compounds of alcohol type or of thiol type which can be represented by the following formula (Im):

in which formula (Im):
  $R^{33}$ represents a hydrocarbon group having from 1 to 20 atoms and has the meaning given for $R^{11}$ or $R^{12}$ in the formula (Ia); and
  Z represents a group of $OM^1$ or $SW^1$ type, in which $M^1$ represents a hydrogen atom or a metal cation, preferably an alkali metal cation.

The preferred compounds correspond to the formula (Im) in which $R^{33}$ represents a hydrocarbon group having from to 20 carbon atoms which can be a saturated or unsaturated and linear or branched acyclic aliphatic group, a saturated, unsaturated or aromatic and monocyclic or polycyclic carbocyclic or heterocyclic group, or any sequence of two or more of the abovementioned groups.

More specifically, $R^{33}$ preferably represents a saturated, linear or branched, acyclic aliphatic group preferably having from 1 to 12 carbon atoms and more preferably from 1 to 4 carbon atoms.

The invention does not exclude the presence of an unsaturation in the hydrocarbon chain, such as one or more double and/or triple bonds, which can be conjugated or nonconjugated.

As mentioned for $R^{11}$ defined in the formula (Ia), the hydrocarbon chain can optionally be interrupted by a heteroatom or a functional group or carry one or more substituents.

In the formula (Im), $R^{33}$ can also represent a saturated or unsaturated carbocyclic group preferably having 5 or 6 carbon atoms in the ring, a saturated or unsaturated heterocyclic group comprising in particular 5 or 6 atoms in the ring, including 1 or 2 heteroatoms, such as nitrogen, sulfur, oxygen or phosphorus atoms, a monocyclic aromatic carbocyclic or heterocyclic group, preferably phenyl, pyridyl, furyl, pyranyl, thiophenyl, thienyl, phospholyl, pyrazolyl, imidazolyl or pyrrolyl, or a fused or nonfused polycyclic aromatic carbocyclic or heterocyclic group, preferably naphthyl.

Provided that $R^{33}$ comprises a ring, the latter can also be substituted. The substituent can have any nature insofar as it does not interfere with the main reaction. The number of substituents is generally at most 4 per ring but is most often equal to 1 or 2.

Reference may be made to the definition of $R^{32}$ in the formula (Ik).

The invention is also targeted at the case where $R^{33}$ comprises a sequence of aliphatic and/or cyclic, carbocyclic and/or heterocyclic groups.

An acyclic aliphatic group can be connected to a ring via a valence bond, a heteroatom or a functional group, such as oxy, carbonyl, carboxyl, sulfonyl, and the like.

A more particular target is cycloalkylalkyl, for example cyclohexylalkyl, groups or aralkyl groups having from 7 to 12 carbon atoms, in particular benzyl or phenylethyl groups.

The invention is also targeted at a sequence of carbocyclic and/or heterocyclic groups and more particularly a sequence of phenyl groups separated by a valence bond or an atom or functional group, such as oxygen, sulfur, sulfo, sulfonyl, carbonyl, carbonyloxy, imino, carbonylimino, hydrazo, or ($C_1$-$C_{10}$, preferably $C_1$-$C_6$) alkylenediimino.

The saturated or unsaturated and linear or branched acyclic aliphatic group can optionally carry a cyclic substituent. "Ring" is understood to mean a saturated, unsaturated or aromatic carbocyclic or heterocyclic ring.

The preferred compounds of formula (Im) correspond more particularly to the general formula ($Im_1$):

in which:
  D symbolizes the residue of a monocyclic or polycyclic aromatic carbocyclic group or a divalent group composed of any sequence of two or more monocyclic aromatic carbocyclic groups;

$R^{34}$ represents one or more identical or different substituents;

Z represents a group of $OM^1$ or $SM^1$ type in which $M^1$ represents a hydrogen atom or a metal cation, preferably an alkali metal cation; and n' represents 0, 1, 2, 3', 4 or 5.

Reference may be made, as examples of $R^{34}$ substituents, to those identified under $R^{32}$ defined in the formula (Ik).

Use is more particularly made, among the compounds of formula ($Im_1$), of those for which the (D) residue represents:

a monocyclic or polycyclic aromatic carbocyclic group with rings which can form, with one another, an ortho-fused system corresponding to the formula ($F_{11}$):

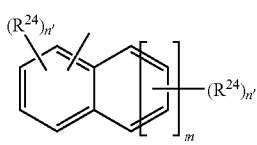

(F₁₁)

in said formula ($F_{11}$), m represents a number equal to 0, 1 or 2, the $R^{34}$ and n' symbols, which are identical or different, having the meanings given above;

a group composed of a sequence of two or more monocyclic aromatic carbocyclic groups corresponding to the formula ($F_{12}$):

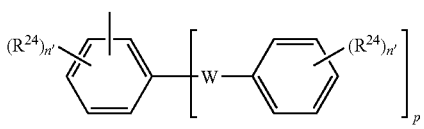

(F₁₂)

in said formula ($F_{12}$), the $R^{34}$ and n' symbols, which are identical or different, have the meanings given above, p is a number equal to 0, 1, 2 or 3 and W represents a valence bond, a $C_1$ to $C_4$ alkylene or alkylidene group, preferably a methylene or isopropylidene group, or a functional group, such as oxy, carbonyl, carboxyl, sulfonyl and others.

The compounds of formula (Im) employed preferably correspond to the formulae ($F_{11}$) and ($F_{12}$), in which:

$R^{34}$ represents a hydrogen atom, a hydroxyl group, a —CHO group, an —$NO_2$ group or a linear or branched alkyl or alkoxy group having from 1 to 6 carbon atoms, preferably from 1 to 4 carbon atoms, more preferably methyl, ethyl, methoxy or ethoxy;

W symbolizes a valence bond, an alkylene or alkylidene group having from 1 to 4 carbon atoms, or an oxygen atom;

m is equal to 0 or 1;

n' is equal to 0, 1 or 2; and p is equal to 0 or 1.

Mention may more particularly be made, by way of illustration of compounds corresponding to the formula (Im), of:

those in which the D residue corresponds to the formula ($F_{11}$) in which m and n' are equal to 0, such as phenol or thiophenol;

those in which the D residue corresponds to the formula ($F_{11}$) in which m is equal to 0 and n' is equal to 1, such as hydroquinone, pyrocatechol, resorcinol, alkylphenols, alkylthiophenols, alkoxyphenols, salicylaldehyde, para-hydroxybenzaldehyde, methyl salicylate, the methyl ester of para-hydroxybenzoic acid, chlorophenols, nitrophenols or para-acetamidophenol;

those in which the D residue corresponds to the formula ($F_{11}$) in which m is equal to 0 and n' is equal to 2, such as dialkylphenols, vanillin, isovanillin, 2-hydroxy-5-acetamidobenzaldehyde, 2-hydroxy-5-propionamidobenzaldehyde, 4-allyloxybenzaldehyde, dichlorophenols, methylhydroquinone or chlorohydroquinone;

those in which the D residue corresponds to the formula ($F_{11}$) in which m is equal to 0 and n' is equal to 3, such as 4-bromovanillin, 4-hydroxyvanillin, trialkylphenols, 2,4,6-trinitrophenol, 2,6-dichloro-4-nitrophenol, trichlorophenols, dichlorohydro-quinones or 3,5-dimethoxy-4-hydroxybenzaldehyde;

those in which the D residue corresponds to the formula ($F_{11}$) in which m is equal to 1 and n' is greater than or equal to 1, such as dihydroxy-naphthalene, 4-methoxynaphth-1-ol or 6-bromonaphth-2-ol;

those in which the D residue corresponds to the formula ($F_{12}$) in which p is equal to 1 and n' is greater than or equal to 1, such as 2-phenoxyphenol, 3-phenoxyphenol, phenylhydroquinone, 4,4'-dihydroxy-biphenyl, 4,4'-isopropylidenediphenol (bisphenol A), bis(4-hydroxyphenyl)methane, bis(4-hydroxyphenyl) sulfone, bis(4-hydroxyphenyl) sulfoxide or tetra-bromobisphenol A.

Mention may be made, among the other nucleophilic compounds belonging to completely different families which are capable of being employed in the process of the invention, of the compounds comprising phosphorus and the compounds comprising phosphorus and nitrogen, preferably those corresponding to the following formulae:

phosphides of formula $(R^{35})_2$—$P^-$  (In);

phosphines of formula $(R^{35})_3$—P  (Io);

phosphonium azayldiides of formula $(R^{35})_3$—$P^+$—$N^2$  (Ip);

phosphonium azaylides of formula $(R^{35})_3$—$P^+$—N—$R^{36}$  (Iq);

in which formulae (In) to (Iq), the $R^{35}$ groups, which are identical or different, and the $R^{36}$ group represent:

$C_1$-$C_{12}$ alkyl;

$C_5$-$C_6$ cycloalkyl;

$C_5$-$C_6$ cycloalkyl substituted by one or more $C_1$-$C_4$ alkyl groups or $C_1$-$C_4$ alkoxy groups;

phenylalkyl, the aliphatic part of which has from 1 to 6 carbon atoms;

phenyl; or phenyl substituted by one or more $C_1$-$C_4$ alkyl groups or $C_1$-$C_4$ alkoxy groups or by one or more halogen atom(s).

Mention may be made, as particularly preferred phosphorus-comprising compounds, of tricyclohexylphosphine, trimethylphosphine, triethylphosphine, tri-(n-butyl)phosphine, tri(isobutyl)phosphine, tri(tert-butyl)phosphine, tribenzylphosphine, dicyclohexyl-phenylphosphine, triphenylphosphine, dimethylphenyl-phosphine, diethylphenylphosphine or di(tert-butyl)-phenylphosphine.

Other compounds capable of being used in the process of the invention are the hydrocarbon derivatives comprising a nucleophilic carbon.

Mention may more particularly be made of the anions of malonate type comprising an —OOC—$HC^-$—COO— group.

Mention may be made of the alkyl malonate anions of formula (Ir):

$R^{37}$—OOC—$HC^-(R^{38})$—COO—$R'^{37}$  (Ir)

in which:

R$^{37}$ and R$^{'37}$, which are identical or different, represent an alkyl group comprising from 1 to 12 atoms, preferably from 1 to 4 atoms;

R$^{38}$ is selected from a hydrogen atom; $C_1$-$C_{12}$ alkyl; $C_5$-$C_6$ cycloalkyl; $C_5$-$C_6$ cycloalkyl substituted by one or more $C_1$-$C_4$ alkyl or $C_1$-$C_4$ alkoxy; phenyl; phenyl substituted by one or more $C_1$-$C_4$ alkyls or $C_1$-$C_4$ alkoxy or by one or more halogen atoms; or phenylalkyl, the aliphatic part of which comprises from 1 to 6 carbon atoms.

Mention may also be made of the anions of malononitrile and malonodinitrile type comprising an R$^{37}$—OOC—HC$^-$(R$^{38}$)—ON or NC—HC$^-$—CN group respectively, in which R$^{37}$ and R$^{38}$ have the meanings given above.

The compounds of nitrile type comprising an R$^{'28}$—CN group, in which R$^{'28}$ has any nature and has the meanings given for R$^{11}$ in the formula (Ia) and also represents a metal cation, preferably an alkali metal cation, more preferably still lithium, sodium or potassium, are also suitable.

Mention may be made, as examples of nitriles, of acetonitrile, cyanobenzene, optionally carrying one or more substituents on the benzene ring, or ethanal cyanohydrin CH$_3$CH(OH)CN.

Also capable of being employed in the process of the invention are the compounds of acetylenide type, which can be represented schematically by the formula (Is):

$$R^{39}—C\equiv C^- \quad (Is)$$

in said formula, R$^{39}$ has any nature and has in particular the meanings given for R$^{11}$ in the formula (Ia), and the counterion is a metal cation, preferably sodium or potassium.

Mention may be made, as more specific examples, of sodium acetylide, potassium acetylide, sodium diacetylide or potassium diacetylide.

Mention may be made, as other categories of nucleophilic compounds which can be employed in the process of the invention, of the compounds of profen type and their derivatives, which can be represented by the following formula (It):

$$R^{40}—HC^-—COO—R^{41} \quad (It)$$

in which formula:

R$^{40}$ has the meanings given for R$^{11}$ in the formula (Ia); and

R$^{41}$ represents an alkyl group having from 1 to 12 carbon atoms, preferably from 1 to 4 atoms.

The preferred compounds are those which correspond to the formula (It) in which R' represents an alkyl group having from 1 to 12 carbon atoms, a cycloalkyl group having 5 or 6 carbon atoms and an aryl group having 6 or 12 carbon atoms, or a nitrogenous heterocycle having 5 or 6 atoms.

Mention may also be made, as nucleophilic compounds, of those comprising a carbanion and for which the counterion is a metal, corresponding to the following formulae:

(Iu$_1$)

(Iu$_2$)

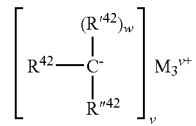

(Iu$_3$)

in which:

the R$^{42}$ group represents:

an alkyl group having from 1 to 12 carbon atoms;

a cycloalkyl group having 5 or 6 carbon atoms;

a cycloalkyl group having 5 or 6 carbon atoms substituted by one or more alkyl radicals having 1 to 4 carbon atoms and/or one or more alkoxy radicals having from 1 to 4 carbon atoms;

a phenylalkyl group, the aliphatic part of which comprises from 1 to 6 carbon atoms;

a phenyl group;

a phenyl group substituted by one or more alkyl radicals having from 1 to 4 carbon atoms or one or more alkoxy radicals having from 1 to 4 carbon atoms or by one or more halogen atoms; or a saturated, unsaturated or aromatic heterocyclic group preferably comprising 5 or 6 atoms and comprising, as heteroatom(s), sulfur, oxygen or nitrogen;

the R$^{'42}$ and R$^{''42}$ groups represent a hydrogen atom or a group such as R$^{42}$;

two of the R$^{42}$, R$^{'42}$ and R$^{''42}$ groups can be connected together to form a saturated, unsaturated or aromatic carbocycle or heterocycle preferably having 5 or 6 carbon atoms;

M$_2$ represents a metal element from Group Ia of the Periodic Table of the Elements;

M$_3$ represents a metal element from Groups IIa and IIb of the Periodic Table of the Elements;

X$_1$ represents a chlorine or bromine atom;

v is the valency of the metal M$_3$; and w is equal to 0 or 1.

In the present text, reference is made, above and in the continuation, to the Periodic Table of the Elements published in the Bulletin de la Société Chimique de France, No. 1 (1966).

Among the compounds of formulae (Iu$_1$) to (Iu$_3$), those which are preferred involve, as metals, lithium, sodium, magnesium or zinc and X$_1$ represents a chlorine atom.

The R$^{42}$, R$^{'42}$ and R$^{''42}$ groups are advantageously a $C_1$-$C_4$ alkyl group, a cyclohexyl group or a phenyl group or said groups can form a benzene, cyclopentadiene, pyridine or thiophene ring.

Mention may be made, as examples, of n-butyllithium, t-butyllithium, phenyllithium, methyl- or ethyl- or phenylmagnesium bromide or chloride, diphenylmagnesium, dimethyl- or diethylzinc, cyclopentadienylzinc, or ethylzinc chloride or bromide.

Recourse may be had, as other nucleophilic compounds capable of being employed, to boronic acids or their derivatives and more particularly to those corresponding to the following formula (Iv):

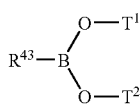

(Iv)

in which:
R[43] represents a monocyclic or polycyclic, aromatic, carbocyclic or heterocyclic group; and
T[1] and T[2], which are identical or different, represent a hydrogen atom, a saturated or unsaturated and linear or branched aliphatic group having from 1 to 20 carbon atoms or an R[43] group.

More specifically, the boronic acid or its derivative, corresponds to the formula (Iv) in which the R[43] group represents an aromatic carbocyclic or heterocyclic group. Thus, R[43] can take the meanings given above for D in the formula (Im₁). However, R[43] more particularly represents a carbocyclic group, such as a phenyl or naphthyl group, or a heterocyclic group, such as a pyrrolyl, pyridyl, pyrimidinyl, pyridazinyl, pyrazinyl, 1,3-thiazolyl, 1,3,4-thiadiazolyl or thienyl group.

The aromatic ring can also be substituted. The number of substituents is generally at most 4 per ring but is most often equal to 1 or 2. Reference may be made to the definition of R[32] of the formula (Ik) for examples of substituents.

The preferred substituents are alkyl or alkoxy groups having from 1 to 4 carbon atoms, an amino group, a nitro group, a cyano group, a halogen atom or a trifluoromethyl group.

As regards T[1] and T[2], which can be identical or different, they more particularly represent a hydrogen atom or a linear or branched acyclic aliphatic group which has from 1 to 20 carbon atoms and which is saturated or comprises one or more unsaturations in the form of double and/or triple bond(s) in the chain, preferably from 1 to 3 unsaturations, which are preferably simple or conjugated double bonds.

T[1] and T[2] preferably represent an alkyl group having from 1 to 10 carbon atoms, preferably from 1 to 4 carbon atoms, or an alkenyl group having from 2 to 10 carbon atoms, preferably a vinyl or 1-methylvinyl group.

T[1] and T[2] can additionally take the meanings given for R[43] and in particular any ring can also carry a substituent as described above.

R[43] preferably represents a phenyl group.

It will not be departing from the scope of the present invention to resort to boronic acid derivatives, such as anhydrides and esters, more particularly alkyl esters having from 1 to 4 carbon atoms.

Mention may in particular be made, as examples of arylboronic acids, of benzeneboronic acid, 2-thiopheneboronic acid, 3-thiopheneboronic acid, 4-methylbenzeneboronic acid, 3-methylthiophene-2-boronic acid, 3-aminobenzeneboronic acid, 3-aminobenzeneboronic acid hemisulfate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid and the esters and anhydrides of these acids.

The present description provides lists of nucleophilic compounds but are not under any circumstances limiting and any type of nucleophilic compound can be envisaged.

As indicated above and according to the process of the present invention, a —C—C— or —C—HE- bond (where HE represents O, S, P, N, Si, B and the like) can be created by reaction of a nucleophilic compound, such as those which have just been described above, with a compound carrying a leaving group, in particular a compound comprising an unsaturated bond situated in the α position with respect to a leaving group.

More specifically, the compound carrying a leaving group is represented by the general formula (II):

in which formula R⁰ represents a hydrocarbon group comprising from 2 to 20 carbon atoms and optionally has at least one unsaturation (a double or triple bond) situated in the a position with respect to a leaving group X or represents a monocyclic or polycyclic aromatic carbocyclic and/or heterocyclic group.

In accordance with the process of the invention, the compound of formula (I) is reacted with a compound of formula (II) in which:
R⁰ represents an aliphatic hydrocarbon group optionally comprising a double bond and/or a triple bond in the a position with respect to the leaving group or a cyclic hydrocarbon group comprising an unsaturation carrying the leaving group; or
R⁰ represents a monocyclic or polycyclic aromatic carbocyclic and/or heterocyclic group;
X represents a leaving group, preferably a halogen atom or a sulfonic ester group of formula —OSC₂—R[e], in which R[e] is a hydrocarbon group.

The compound of formula (II) will be subsequently denoted by "compound carrying a leaving group".

In the formula of the sulfonic ester group, R[e] is a hydrocarbon group of any nature. However, given that X is a leaving group, it is advantageous from an economic viewpoint for R[e] to be simple in nature and to more particularly represent a linear or branched alkyl group having from 1 to 4 carbon atoms, preferably a methyl or ethyl group; however, it can also represent, for example, a phenyl or tolyl group or a trifluoromethyl group.

Among the X groups, the preferred group is a triflate group, which corresponds to an R[e] group representing a trifluoromethyl group.

The choice is preferably made, as preferred leaving groups, of a bromine or chlorine atom.

The compounds of formula (II) very particularly targeted according to the process of the invention can be categorized into three groups:
(1) the compounds of aliphatic type carrying a double bond and which can be represented by the formula (IIa):

in which:
R[44], R[45] and R[46], which are identical or different, represent a hydrogen atom or a hydrocarbon group having from 1 to 20 carbon atoms which can be a saturated or unsaturated and linear or branched aliphatic group, a saturated, unsaturated or aromatic and monocyclic or polycyclic carbocyclic or heterocyclic group, or any sequence of aliphatic and/or carbocyclic and/or heterocyclic group(s) as mentioned above; and X symbolizes the leaving group as defined above;

(2) compounds of aliphatic type carrying a triple bond and which can be represented by the formula (IIb):

in which:

$R^{44}$ has the meanings given in the formula (IIa); and

X represents a leaving group as defined above;

(3) compounds of aromatic type which are subsequently denoted by "haloaromatic compound" and which can be represented by the formula (IIc):

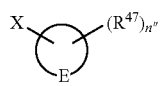

in which:

E symbolizes the residue of a ring forming all or part of a monocyclic or polycyclic, aromatic, carbocyclic and/or heterocyclic system;

$R^{47}$, which are identical or different, represent substituents on the ring;

X represents a leaving group as defined above; and n" represents the number of substituents on the ring.

The invention applies to the unsaturated compounds corresponding to the formulae (IIa) and (IIb) in which $R^{44}$ preferably represents a saturated and linear or branched acyclic aliphatic group preferably having from 1 to 12 carbon atoms.

The invention does not rule out the presence of another unsaturated bond in the hydrocarbon chain, such as a triple bond or else one or more double bonds, which can be conjugated or nonconjugated.

The hydrocarbon chain can optionally be interrupted by a heteroatom (for example oxygen or sulfur) or by a functional group, insofar as the latter does not react, and mention may be made in particular of a group such as especially —CO—.

The hydrocarbon chain can optionally carry one or more substituents insofar as they do not react under the reaction conditions and mention may in particular be made of a halogen atom, a nitrile group or a trifluoromethyl group.

The saturated or unsaturated and linear or branched acyclic aliphatic group can optionally carry a cyclic substituent. "Ring" is understood to mean a saturated, unsaturated or aromatic, carbocyclic or heterocyclic ring.

The acyclic aliphatic group can be connected to the ring via a valence bond, a heteroatom or a functional group, such as oxy, carbonyl, carboxy, sulfonyl, and the like.

It is possible to envisage, as examples of cyclic substituents, cycloaliphatic, aromatic or heterocyclic substituents, in particular cycloaliphatic substituents comprising 6 carbon atoms in the ring, or benzene substituents, these cyclic substituents themselves optionally carrying any substituent, insofar as they do not interfere in the reactions occurring in the process of the invention. Mention may in particular be made of alkyl or alkoxy groups having from 1 to 4 carbon atoms.

Among aliphatic groups carrying a cyclic substituent, the aralkyl groups having from 7 to 12 carbon atoms, in particular the benzyl or phenylethyl groups, are more particularly targeted.

In the formulae (IIa) and (IIb), $R^{44}$ can also represent a saturated or unsaturated carbocyclic group preferably having 5 or 6 carbon atoms in the ring, preferably a cyclohexyl group, a saturated or unsaturated heterocyclic group comprising in particular 5 or 6 atoms in the ring, including one or two heteroatoms, such as nitrogen, sulfur and oxygen atoms, a monocyclic aromatic carbocyclic group, preferably a phenyl group, or a fused or nonfused polycyclic aromatic carbocyclic group, preferably a naphthyl group.

With regard to $R^{45}$ and $R^{46}$, they preferably represent a hydrogen atom or an alkyl group having from 1 to 12 carbon atoms, a phenyl group or an aralkyl group having from 7 to 12 carbon atoms, preferably a benzyl group.

In the formulae (IIa) and/or (IIb), $R^{44}$, $R^{45}$ and $R^{46}$ more particularly represent a hydrogen atom or else $R^{44}$ represents a phenyl group and $R^{45}$ and $R^{46}$ represent a hydrogen atom.

It should be noted that $R^{34}$ and $R^{35}$ can also represent a functional group, insofar as they do not interact in the coupling reaction. Mention may be made, as examples of such functional groups, of the amido, ester, ether or cyano groups.

Mention may in particular be made, as examples of compounds corresponding to the formulae (IIa) and (IIb), of vinyl chloride or vinyl bromide, or β-bromostyrene or β-chlorostyrene, or bromoalkyne or iodoalkyne.

The invention applies in particular to the haloaromatic compounds corresponding to the formula (IIc) in which E is the residue of an optionally substituted cyclic compound preferably having at least 4 atoms in the ring, preferably 5 or 6 atoms, and representing at least one of the following rings:

a monocyclic aromatic carbocycle or a polycyclic aromatic carbocycle, that is to say a compound composed of at least two aromatic carbocycles which form, with one another, ortho- or ortho- and peri-fused systems or a compound composed of at least two carbocycles, only one of which among them is aromatic, which form, with one another, ortho- or ortho- and peri-fused systems;

a monocyclic aromatic heterocycle comprising at least one of the heteroatoms P, O, N and/or S or a polycyclic aromatic heterocycle, that is to say a compound composed of at least two heterocycles comprising at least one heteroatom in each ring, at least one of the two rings of which is aromatic, which form, with one another, ortho- or ortho- and peri-fused systems, or a compound composed of at least one carbocycle and at least one heterocycle, at least one of the rings of which is aromatic, which form, with one another, ortho- or ortho- and peri-fused systems.

More particularly, the optionally substituted residue E preferably represents the residue of an aromatic carbocycle, such as benzene, of an aromatic bicycle comprising two aromatic carbocycles, such as naphthalene, or of a partially aromatic bicycle comprising two carbocycles, one of the two of which is aromatic, such as 1,2,3,4-tetrahydronaphthalene.

The invention also envisages the fact that E can represent the residue of a heterocycle insofar as it is more electrophilic than the compound corresponding to the formula (Ik).

Mention may be made, as specific examples, of an aromatic heterocycle, such as furan or pyridine, an aromatic bicycle comprising an aromatic carbocycle and an aromatic heterocycle, such as benzofuran or benzopyridine, a partially aromatic bicycle comprising an aromatic carbocycle and a heterocycle, such as methylenedioxybenzene, an aromatic bicycle comprising two aromatic heterocycles, such as 1,8- naphthylpyridine, or a partially aromatic bicycle comprising a carbocycle and an aromatic heterocycle, such as 5,6,7,8-tetrahydroquinoline.

In the process of the invention, use is preferably made of a haloaromatic compound of formula (IIc) in which E represents an aromatic nucleus, preferably a benzene or naphthalene nucleus.

The aromatic compound of formula (IIc) can carry one or more substituents.

In the present text, "more" is understood to mean generally less than four $R^{47}$ substituents on an aromatic nucleus. Reference may be made to the definitions of the $R^{42}$ group in the formula (Ik) for various examples of substituents.

$R^{47}$ can also represent a saturated, unsaturated or aromatic heterocycle comprising 5 or 6 atoms and comprising sulfur, oxygen and/or nitrogen as heteroatom(s). In this respect, mention may in particular be made of the pyrazolyl or imidazolyl groups.

In the formula (IIc), n" is equal to 0, 1, 2, 3 or 4, preferably equal to 1 or 2.

Mention may in particular be made, as examples of compounds corresponding to the formula (IIc), of para-chlorotoluene, para-bromoanisole or para-bromo-trifluorobenzene.

The amount of the compound carrying a leaving group of formula (II), preferably of formula (IIa) or (IIb) or (IIc), employed is generally expressed with respect to the amount of nucleophilic compound and can vary within wide proportions; generally, it is in the vicinity of stoichiometry.

Thus, the ratio of the number of moles of the compound carrying the leaving group to the number of moles of the nucleophilic compound generally varies between 0.1 and 2.0, preferably between 0.5 and 1.5, more preferably between 0.8 and 1.2 and more preferentially between 0.9 and 1.1.

In accordance with the process of the invention, the nucleophilic compound, preferably corresponding to the formulae (Ia) to (Iv), is reacted with a compound carrying a leaving group, preferably corresponding to the formula (II), more preferably to the formulae (IIa) or (IIb) or (IIc), in the presence of an effective amount of a catalytic system comprising a copper/cyclovinyl phosphine complex as defined according to the invention.

This is because it has been discovered that it is possible to carry out coupling reactions, such as defined supra, between nucleophilic compounds and compounds carrying a leaving group by using a catalytic system comprising a copper/cyclovinyl phosphine complex as defined according to the invention.

Mention may be made, as examples of catalytic systems capable of being employed, of those comprising at least one copper/cyclovinyl phosphine complex, such as those defined supra under the generic term Pho-CyV/Cu, that is to say complexes of copper with at least one cyclovinyl phosphine of formula (1) as defined above.

Mention may be made, as example of complex of Pho-CyV/Cu type particularly suitable for the coupling reactions defined above, of the pyridylvinyldiphenylphosphine/copper iodide monomer complex [Py-CH=CH—PPh$_2$]$_2$CuI, where Ph represents the phenyl radical. As also indicated above, the Pho-CyV/Cu complex can be prepared in situ, in the reaction medium for the coupling reaction.

The total amount of copper/cyclovinyl phosphine complex catalyst employed in the process of the invention, expressed by the molar ratio of the number of moles of complex, expressed as copper, to the number of moles of compound carrying a leaving group, generally varies between 0.001 and 0.5, preferably between 0.01 and 0.1.

According to an alternative form, the invention does not exclude the copper being combined with a small amount of another metal element denoted by M. The metal element M is selected from Group VIII, Ib and IIb of the Periodic Table of the Elements, as defined above.

Mention may be made, as examples of metals M, of silver, palladium, cobalt, nickel, iron and/or zinc.

Use is advantageously made of a mixture comprising palladium and copper. The palladium can be introduced in the form of a finely divided metal or in the form of an inorganic derivative, such as an oxide or a hydroxide. It is possible to resort to an inorganic salt, preferably nitrate, sulfate, oxysulfate, halide, oxyhalide, silicate or carbonate, or to an organic derivative, preferably cyanide, oxalate, acetyl-acetonate, alkoxide, more preferably still methoxide or ethoxide, or carboxylate, more preferably still acetate.

It is also possible to employ complexes, in particular chlorine- or cyanide-comprising complexes, of palladium and/or of alkali metals, preferably sodium or potassium, or of ammonium. Mention may in particular be made, as examples of compounds capable of being employed in the preparation of the catalysts of the invention, of palladium(II) bromide, palladium(II) chloride, palladium(II) iodide, palladium(II) cyanide, palladium(II) nitrate hydrate, palladium(II) oxide, palladium(II) sulfate dihydrate, palladium(II) acetate, palladium (II) propionate, palladium(II) butyrate or palladium benzoate.

Mention may be made, as specific examples of nickel derivatives, of nickel(II) halides, such as nickel(II) chloride, bromide or iodide, nickel(II) sulfate, nickel(II) carbonate, salts of organic acids comprising from 1 to 18 carbon atoms, such as, in particular, acetate or propionate, nickel(II) complexes, such as nickel(II) acetylacetonate, dibromobis(triphenyl-phosphine)nickel(II) or dibromobis(bipyridine)-nickel (II), or nickel(0) complexes, such as bis(1,5-cyclooctadiene) nickel(0) or [bis(diphenylphosphino)-ethane]nickel(0).

Recourse may also be had to derivatives based on iron or on zinc, generally in the oxide or hydroxide form or in the form of salts, such as halides, preferably chloride, nitrates and sulfates.

The amount of the metal element M represents less than 50 mol %, preferably less than 25 mol %, advantageously less than 10 mol %, with respect to the number of moles of copper.

More preferably still, use is made of a catalyst in the form of a complex with a cyclovinyl phosphine comprising only copper.

A base, the function of which is to scavenge the leaving group, is also involved in the process of the invention.

The bases suitable for the process of the invention can be characterized by their pKa, which is advantageously at least greater than or equal to 2, preferably between 4 and 30.

The pKa is defined as the ionic dissociation constant of the acid/base pair when water is used as solvent. Reference may be made, for the choice of a base having a pKa as defined by the invention, inter alia, to the Handbook of Chemistry and Physics, 66$^{th}$ edition, pp. D-161 and D-162.

Mention may be made, among the bases which can be used, inter alia, of inorganic bases, such as carbonates, hydrogen carbonates, phosphates or hydroxides of alkali metals, preferably sodium, potassium or cesium, or of alkaline earth metals, preferably calcium, barium or magnesium.

Recourse may also be had to alkali metal hydrides, preferably sodium hydride, or to alkali metal alkoxides, preferably sodium alkoxides or potassium alkoxides, and more preferably to sodium methoxide, ethoxide or tert-butoxide.

Organic bases, such as tertiary amines, are also suitable and mention may more particularly be made of triethylamine, tri(n-propyl)amine, tri(n-butyl)amine, methyldibutylamine, methyldicyclohexylamine, ethyldiisopropylamine, N,N-diethylcyclohexylamine, pyridine, 4-(dimethylamino)pyridine, N-methylpiperidine, N-ethylpiperidine, N-(n-butyl)piperidine, 1,2-dimethylpiperidine, N-methylpyrrolidine and 1,2-dimethylpyrrolidine.

The choice is preferably made, among the bases, of alkali metal carbonates.

The amount of base employed is such that the ratio of the number of moles of base to the number of moles of the compound carrying the leaving group preferentially varies between 1 and 4, preferably in the vicinity of 2.

The coupling reaction, in particular arylation or vinylation or alkynylation reaction, carried out according to the invention is generally carried out in the presence of an organic solvent. Recourse is preferably had to an organic solvent which does not react under the conditions of the reaction.

Recourse is preferably had, as types of solvents employed in the process of the invention, to a polar organic solvent and preferably a polar aprotic organic solvent.

Nonlimiting examples of solvents which can be employed in the process of the invention are selected from:
- linear or cyclic carboxamides, such as N,N-dimethylacetamide (DMAC), N,N-diethylacetamide, dimethylformamide (DMF), diethylformamide or 1-methyl-2-pyrrolidinone (NMP);
- dimethyl sulfoxide (DMSO);
- hexamethylphosphotriamide (HMPT);
- tetramethylurea;
- nitro compounds, such as nitromethane, nitroethane, 1-nitropropane, 2-nitropropane and their mixtures, or nitrobenzene;
- aliphatic or aromatic nitriles, such as acetonitrile, propionitrile, butanenitrile, isobutanenitrile, pentanenitrile, 2-methylglutaronitrile or adiponitrile;
- tetramethylene sulfone (sulfolane);
- organic carbonates, such as dimethyl carbonate, diisopropyl carbonate or di(n-butyl) carbonate;
- alkyl esters, such as ethyl acetate or isopropyl acetate;
- halogenated or nonhalogenated aromatic hydrocarbons, such as chlorobenzene or toluene;
- ketones, such as acetone, methyl ethyl ketone, methyl isobutyl ketone, cyclopentanone or cyclohexanone;
- nitrogenous heterocycles, such as pyridine, picoline and quinolines.

Use may also be made of a mixture of two or more solvents selected in particular from those listed above.

The preferred solvents are carboxamides, such as DMF, acetonitrile, DMSO, NMP and DMAC.

The amount of organic solvent to be employed is determined according to the nature of the organic solvent selected. It is determined so that the concentration of the compound carrying the leaving group in the organic solvent is preferably between 5% and 40% by weight.

According to an alternative form, the nucleophilic compound and/or the compound carrying the leaving group can be used as solvent(s) for the reaction, in which case it is not necessary to add an additional solvent to the reaction medium.

The coupling reaction, that is to say the reaction for the creation of a C—C or C—HE bond according to the process of the invention, is generally carried out at a temperature which is advantageously situated between 0° C. and 200° C., preferably between 20° C. and 170° C. and more preferably still between 25° C. and 140° C.

Said reaction is generally carried out at atmospheric pressure but higher pressures, which can, for example, reach 10 bar, can also be used.

From a practical viewpoint, the reaction is simple to carry out.

The order in which the reactants are employed is not critical. Preferably, the copper/cyclovinyl phosphine complex catalytic system, the nucleophilic compound, preferably of formula (Ia) to (Iv), the base, the compound carrying the leaving group, preferably of formula (II), more preferably of formula (IIa), (IIb) or (IIc), and optionally the organic solvent are charged. The reaction medium is then brought to the desired temperature.

As mentioned above, it is possible, in an alternative form, to introduce the copper and at least one cyclovinyl phosphine as ligand, in order to form the copper/cyclovinyl phosphine complex in situ.

The progress of the reaction is monitored by following the disappearance of the compound carrying the leaving group. At the end of the reaction, a product of the R-Q-R⁰ type is obtained, R, Q and $R^o$ being as defined above.

The compound obtained is recovered according to the conventional techniques used, in particular by crystallization from an organic solvent.

Mention may in particular be made, as more specific examples of such organic solvents which can be used in the crystallization stage, of aliphatic or aromatic hydrocarbons, which may or may not be halogenated, carboxamides, and nitriles. Mention may in particular be made of cyclohexane, toluene, dimethylformamide, and acetonitrile.

Examples of the implementation of the invention are given below. These examples are given by way of indication, without a limiting nature.

EXAMPLES

In the examples which follow, the analytical techniques below were used.

The proton ($^1$H), phosphorus ($^{31}$P), and carbon ($^{13}$C) NMR spectra were acquired at 20° C. on Brucker AC 200, DRX-250 and DRX-400 spectrometers, in which the fundamental frequencies for $^1$H are 81.01, 200.13, and 400.13 MHz respectively. The chemical shifts of $^1$H, $^{31}$P, and $^{13}$C, expressed in ppm, are referred to relative to the signal for tetramethylsilane (TMS). Excluding special cases, the $^{13}$C spectra were recorded with irradiation of the hydrogens. The coupling constants are expressed in Hz.

The $^1$H NMR spectra are presented as follows: scale δ (ppm), (multiplicity, number of hydrogen atoms, attribution, coupling constant in Hz). The numbers carried by the hydrogen atoms in the indexations are those of the carbon atoms to which they are bonded. The multiplicities are indicated, when the spectra are of the first order, in the form of abbreviations, which may be combined with one another (s=singlet, d=doublet, t=triplet, q=quadruplet, quint.=quintuplet, sext.=sextuplet, sept.=septuplet, m=multiplet). The multiplicity of the $^{13}$C NMR signals is indicated only when the signal is not present in the form of a singlet (C—P coupling, for example).

The GC/MS analyses were carried out on an Agilent Technologies 6890 N chromatograph coupled to an Agilent 5973 N high-energy dynode mass detector (quadripolar filter, ionization mode: electron impact), with an apolar capillary column HP5-MS (length 30 m, internal diameter 0.25 mm, 5% diphenyldimethylpolysiloxane film with a thickness of 0.25 μm).

The analytical conditions are as follows: injector temperature: 250° C., interface temperature: 280° C., ion source: 230° C., quadrupole detector: 150° C., carrier gas: helium (0.5 bar).

The IR spectra were recorded on a Nicolet 210 Fourier-transform spectrophotometer (DTGS detector). The solid products were analyzed in the form of KBr disks. The liquid products were recorded as a film deposited between two KBr disks or in the form of a solution injected into a cell. The intensity of the absorption peak of maximum intensity is set arbitrarily at 100% transmittance. The intensity of the other bands is estimated relative to the latter; it is denoted by the following abbreviations: SS (very strong: 80 to 100% of the intensity of the absorption peak of maximum intensity), S (strong: 60 to 80%), m (moderate: 40 to 60%), w (weak: 20 to 40%) or ww (very weak: 0 to 20%).

The low-resolution mass spectrometry analyses and MSMS analyses were performed on a JEOL JMS-DX300 spectrometer (ionization mode: FAB, acceleration voltage: 3 Kev, ionizing gas: xenon) or on a Micro-Mass instrument (Q-TOF detector, ES+ mode, cone voltage: 2 to 30 V, collision voltage: 25 V).

The melting points, which are given without correction, were determined on a Büchi B-540 melting point capillary apparatus.

The thin-film chromatographs were produced on aluminum plates coated with alumina (neutral, type E) or with Merck 60 F silica. The Rf values of the isolated products were calculated after elution on a silica plate, unless indicated otherwise.

The chromatographic purifications were carried out by chromatography on a 60 A silica C.C column, SDS (35-70 μm or 70-200 μm) or on Merck 90 alumina (63-200 μm).

Each compound characterized was dried beforehand under vacuum in a dessicator in the presence of phosphoric anhydride. The yields are calculated from samples isolated with a purity of greater than or equal to 97%, as assessed by $^1$H NMR and GC.

All of the reagents whose synthesis is not described here were obtained from commercial sources (Aldrich, Acros, Avocado, Fluka, Lancaster, Strem).

Examples A

Syntheses of phosphonium salts

The reactions are carried out under a pure and dry nitrogen atmosphere. A solution of 26.5 g (0.1 mol) of triphenylphosphine in 200 ml of anhydrous tetrahydrofuran (THF) is admixed with 1.4 g (0.2 g at. (gram atom)) of lithium. Following overnight stirring at ambient temperature, 9.25 g (11 ml, 0.1 mol) of tert-butyl chloride, diluted in 50 ml of anhydrous THF, are added. The reaction mixture is heated at reflux for an hour. The clear, dark red-colored solution lightens. The temperature is returned to ambient before 0.2 mol of halogen compound, distilled beforehand and diluted in 50 ml of anhydrous THF, is introduced.

The reaction mixture is left with stirring at a temperature θ for a time T (see table 1 below). The phosphonium salt is obtained either by simple filtration or by evaporation of the solvent and then recrystallization to constant melting point, and finally is dried under vacuum at 60° C. in the presence of phosphorus pentoxide ($P_2O_5$).

TABLE 1

Syntheses of phosphonium salts
Reaction conditions and yields

| Halogen compound | θ | T | Phosphonium salt | Yield (%) |
|---|---|---|---|---|
| $CH_3I$ | 20° C. | 24 h | A1 | 96 |
| $CH_3CH_2I$ | 65° C. | 11 h | A2 | 90 |
| $CH_2$=CH—$CH_2I$ | 20° C. | 2 days | A3 | 80 |

The characteristics of the phosphonium salts prepared by the general procedure above are as follows:

Example A1

Dimethyldiphenylphosphonium iodide $C_{14}H_{16}PI$ (342.22), melting point: 255.2° C. (ethanol).
$^{31}P\{^1H\}$ NMR ($CDCl_3$): δ=20.96 (s, 1P).
$^1$H NMR ($CDCl_3$): δ=2.58 (d, 6H, 2$CH_3$, $^2J_{HP}$=14.0 Hz); 7.20-7.80 (m, 10H, 2Ph).
IR (KBr): ν ($cm^{-1}$)=3060 w, 2940 m, 2880 m, 1590 w, 1570 w, 1435 S, 1127-1117 d.S, 975 S, 940 S, 887 S, 790 m, 742 S, 690 S.

Example A2

Diethyldiphenylphosphonium iodide $C_{16}H_{20}PI$ (370.24), melting point: 208.5° C. (ethanol).
$^{31}P\{^1H\}$ NMR ($CDCl_3$): δ=31.84 (s, 1P).
$^1$H NMR ($CDCl_3$): δ=1.27 (td, 6H, 2$CH_3$, $^3J_{HH}$=7.6 Hz, $^3J_{HP}$=20.0 Hz), 3.30 (qd, 4H 2$CH_2$, $^2J_{HP}$=13.2 Hz), 7.60-8.20 (m, 10H, 2Ph).
IR (KBr): ν ($cm^{-1}$)=3010 w, 2940 m, 2990 m, 2905 m, 2880 m, 1590 w, 1585 w, 1480 m, 1430 S, 1115-1110 ep.S, 997 m, 775 S, 742 SS, 749 ep.S, 742 S, 690 S.

Example A3

Diallyldiphenylphosphonium iodide $C_{18}H_{20}PI$ (394.26), melting point: 167.4° C. ($CH_3Cl$/ethyl acetate).
$^{31}P\{^1H\}$ NMR ($CDCl_3$): δ=22.55 (s, 1P).
$^1$H NMR ($CDCl_3$): δ=4.40 (dd, 4H, 2$CH_2$, $^3J_{HH}$=5.0 Hz, $^2J_{HP}$=14.0 Hz), 5.50 (m, 6H, 2CH=$CH_2$), 7.60-8.35 (m, 10H, 2Ph).
IR (KBr): ν ($cm^{-1}$)=3045 ww, 3000 m, 2895 S, 1633 m, 1585 m, 1439-1431 d.S, 1119 S, 1112 ep, 994-990 d.m, 750 S, 690 S.

Examples B

Syntheses of cyclovinyl phosphines

The reactions are carried out under a pure and dry nitrogen atmosphere. A solution of a phosphonium iodide prepared in examples A, in 150 ml of anhydrous tetrahydrofuran (THF), is admixed with two equivalents of n-butyllithium (n-BuLi; 1.6M) at −50° C., and the reaction mixture is then brought to −10° C. over an hour (yellow solution).

At the same temperature, one equivalent of chlorodiphenylphosphine is added. The reaction mixture is left with stirring to return to ambient temperature over an hour (orange solution) and then one equivalent (or more if needed) of α,β-unsaturated, carbonyl-containing cyclic derivative is added. The reaction mixture is kept with stirring at ambient temperature overnight. The THF is then evaporated and the residue is dissolved in dichloromethane.

The organic phase obtained is subsequently washed three times with water, dried over anhydrous magnesium sulfate ($MgSO_4$), and concentrated under vacuum. The products are separated, with satisfactory yields, by chromatography on a silica or alumina column, with a hexane/dichloromethane eluent mixture appropriate for each product.

Example B1

Pyridylvinyldiphenylphosphine (Z)-Py(C$_2$H$_2$) PPh$_2$

The general procedure was followed, using 5 g (14.61 mmol) of dimethyldiphenylphosphonium iodide and 1.4 ml (14.61 mmol) of pyridinecarboxaldehyde (99%). The two isomers are separated on an alumina column with a hexane/dichloromethane eluent (2/1).

The yield of the reaction is 90%. The analyses on the product are given below.

Identification

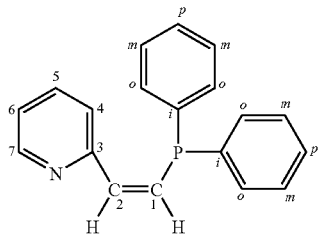 [SMILES: C(=C/P(c1ccccc1)c1ccccc1)/c1ccccn1]

Empirical formula: C$_{19}$H$_{16}$NP.
Molecular weight: 289.16.
Melting point: 106-108° C. (hexane/dichloromethane).
$^{31}$P{$^1$H} NMR (CDCl$_3$): δ=−16.20 (s, 1P).
$^1$H NMR (CDCl$_3$): δ=6.729 (dd, 1H, H$_1$, J$_{H1H2}$=12.4 Hz, J$_{H1P}$=0.6 Hz), 7.054 (ddd, 1H, H$_6$, J$_{H6H7}$=4.8 Hz), 7.330 (dd, 1H, H$_2$, J$_{H2P}$=18.7 Hz), 7.400 (m, 1H, H$_4$, J$_{H4H5}$=7.8 Hz, J$_{H4H6}$=1.2 Hz, J$_{H4H7}$=1.0 Hz), 7.30-7.49 (m, 10H, 2Ph), 7.596 (td, 1H, H$_5$, J$_{H5H6}$=7.5 Hz, J$_{H5H7}$=1.8 Hz), 8.479 (broad d, 1H, H$_7$).
$^{13}$C{$^1$H} NMR (CDCl$_3$): δ=121.79 (d, 1C, C$_6$, J$_{C6P}$=1.5 Hz), 124.10 (d, 1C, C$_4$, J$_{C4P}$=1.6 Hz), 128.10 (s, 1C, C$_p$, J$_{CpP}$=coupling not observed), 128.27 (d, 1C, C$_m$, J$_{CmP}$=7.0), 132.77 (d, 1C, C$_o$, J$_{CoP}$=19.4 Hz), 135.25 (d, 1C, C$_1$, J$_{C1P}$=20.8 Hz), 135.84 (s, 1C, C$_5$, J$_{C5P}$=coupling not observed), 139.81 (d, 1C, C$_2$, J$_{C2P}$=12.4 Hz), 140.50 (d, 1C, C$_1$, J$_{CiP}$=8.8 Hz), 148.60 ppm (s, 1C, C$_7$, J$_{C7P}$=coupling not observed), 154.77 (d, 1C, C$_3$, J$^{C3P}$=2.2 Hz).
IR (KBr): ν (cm$^{-1}$)=3068 m, 3002 m, 1580 S, 1468 S, 1427 SS, 1302 S, 1088 m, 1066 m, 1026 m, 808 SS, 696 SS, 647 S.

Example B2

Pyridylvinyldiphenylphosphine (E)-Py(C$_2$H$_2$) PPh$_2$

Identification

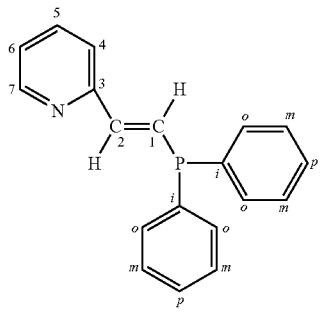 [SMILES: C(=C\P(c1ccccc1)c1ccccc1)/c1ccccn1]

Empirical formula: C$_{19}$H$_{16}$NP.
Molecular weight: 289.16.
$^{31}$P{$^1$H} NMR (CDCl$_3$): δ=−11.04 (ΔW$_{1/2}$=0.9 Hz) (s, 1P).
$^1$H NMR (CDCl$_3$): δ=6.837 (dd, 1H, H$_2$, J$_{H2H1}$=16.8 Hz, J$_{H2P}$=11.2 Hz), 7.172 (ddd, 1H, H$_6$, J$_{H6H7}$=4.8 Hz), 7.248 (ddd, 1H, H$_4$, J$_{H4H5}$=7.9 Hz, J$_{H4H6}$=1.2 Hz, J$_{H4H7}$=1.0 Hz), 7.373-7.518 (m, 10H, 2Ph), 7.553 (dd, 1H, H$_1$, J$_{H1P}$=13.8 Hz), 7.656 (td, 1H, H$_5$, J$_{H5H6}$=7.5 Hz, J$_{H5H7}$=1.9 Hz), 8.601 (ddd, 1H, H$_7$).
$^{13}$C{$^1$H} NMR (CDCl$_3$): δ=122.21 (s, 1C, C$_4$, J$_{C4P}$=coupling not observed), 122.67 (s, 1C, C$_6$, J$_{C6P}$=coupling not observed), 128.62 (d, 1C, C$_m$, J$_{CmP}$=7.1), 128.91 (s, 1C, C$_p$, J$_{CpP}$=coupling not observed), 132.30 (d, 1C, C$_i$, J$_{C1P}$=13.9 Hz), 133.50 (d, 1C, C$_o$, J$_{CoP}$=19.4 Hz), 136.63 (s, 1C, C$_5$, J$_{C5P}$=coupling not observed), 137.15 (d, 1C, C$_i$, J$_{CiP}$=9.3 Hz), 141.32 (d, 1C, C$_2$, J$_{C2P}$=23.5 Hz), 149.71 (s, 1C, C$_7$, J$_{C7P}$=coupling not observed), 154.86 (d, 1C, C$_3$, J$_{C3P}$=11.4 Hz).
IR (KBr): ν (cm$^{-1}$)=3047 m, 3005 m, 1580 S, 1554 m, 1469 SS, 1428 SS, 1305 m, 1149 m, 1178 m, 1149 m, 1094 m, 1024 m, 975 S, 854 m, 763 SS, 749 SS, 742 SS, 694 SS.

Example B3

Myrtenalic phosphine (Z)-C$_3$H$_6$(C$_6$H$_7$)[C$_2$H$_2$]PPh$_2$

The general procedure was followed, using 5 g of dimethyldiphenylphosphonium iodide A1 (14.61 mmol) and 2.4 ml (14.61 mmol) of myrtenal. The two isomers are separated on an alumina column with a hexane/dichloromethane eluent mixture (95/5).

The yield of the reaction is 53% (E/Z=70/30). The analyses on the product are given below.

Identification

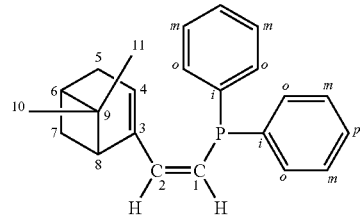 [SMILES: CC1(C)C2CC=C(/C=C\P(c3ccccc3)c3ccccc3)C1C2]

Empirical formula: C$_{23}$H$_{25}$P.
Molecular weight: 332.20.
$^{31}$P{$^1$H} NMR (CDCl$_3$): δ=−23.20 (s, 1P).
$^1$H NMR (CDCl$_3$): δ=0.80 (s, 3H, CH$_3$), 1.28 (s, 3H, CH$_3$), 2.04 (m, 1H, CH), 2.44 (m, 4H, 2CH$_2$), 3.04 (m, 1H, CH), 5.76 (m, 1H, H$_4$), 6.11 (dd, 1H, H$_1$, J$_{H1H2}$=12.64 Hz, J$_{H1P}$=0.77 Hz), 6.78 (dd, 1H, H$_2$, J$_{H2P}$=23.78 Hz), 7.33-7.49 (m, 10H, 2Ph).
$^{13}$C{$^1$H} NMR (CDCl$_3$): δ=20.21 (s, 20, C$_{10-11}$), 40.40 (s, 1C, C$_6$), 45.18 (d, 1C, C$_8$, J$_{C8P}$=12.98 Hz), 31.54 (s, 1C, C$_7$), 32.274 (s, 1C, C$_5$), 38.03 (s, 1C, C$_9$), 125.60 (d, 1C, C$_4$, J$_{C4P}$=15.57 Hz), 128.29 (s, 2C, C$_p$, J$_{CpP}$=coupling not observed), 128.33 (d, 4C, C$_m$, J$_{CmP}$=8.30 Hz), 132.77 (d, 4C, C$_o$, J=CoP=16.10 Hz), 134.22 (d, 1C, C$_1$, J$_{C1P}$=20.72 Hz), 140.42 (d, 2C, C$_i$, J$_{CiP}$=10.30 Hz), 144.44 (d, 1C, C$_2$, J$_{C2P}$=17.31 Hz), 146.70 (d, 1C, C$_3$, J$_{C3P}$=1.26 Hz).
IR (KBr): ν (cm$^{-1}$)=3060 m, 3040 m, 2980 S, 2940 S, 2910 SS, 2820 w, 1600 w, 1580 w, 1470 S, 1430 SS, 1380 m, 1360 m, 1260 w, 1180 w, 1120 w, 1090 m, 1020 S, 1000 m, 970 w, 910 S, 810 m, 730 SS, 695 SS.

Example B4

Myrtenalic phosphine (E)-C$_3$H$_6$(C$_6$H$_7$)[C$_2$H$_2$]PPh$_2$

Identification

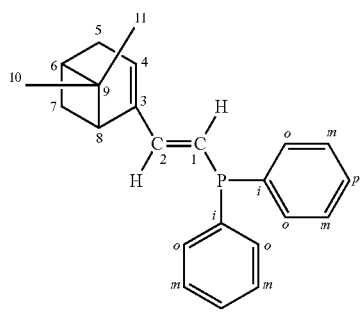 [SMILES: CC1(C)C2CC=C(/C=C/P(c3ccccc3)c3ccccc3)C1C2]

Empirical formula: C$_{23}$H$_{25}$P.
Molecular weight: 332.20.
$^{31}$P{$^1$H} NMR (CDCl$_3$): δ=−12.62 (s, 1P).
$^1$H NMR (CDCl$_3$): δ=0.79 (s, 3H, CH$_3$), 1.38 (s, 3H, CH$_3$), 2.18 (m, 1H, CH), 2.41 (m, 4H, 2CH$_2$), 2.71 (t, 1H, CH), 5.70 (m, 1H, H$_4$), 6.25 (dd, 1H, H$_1$, J$_{H1H2}$=16.85 Hz, J$_{H1P}$=6.32 Hz), 6.70 (dd, 1H, H$_2$, J$_{H2P}$=15.03 Hz), 7.35-7.47 (m, 10H, 2Ph).
$^{13}$C{$^1$H} NMR (CDCl$_3$): δ=22.81 (s, 2C, C$_{11}$), 27.06 (s, 2C, C$_{10}$), 31.44 (s, 1C, C$_7$), 32.23 (s, 1C, c$_5$), 37.93 (s, 1C, C$_9$), 41.05 (s, 1C, C$_6$), 41.53 (s, 1C, c$_8$, J$_{C8P}$=coupling not observed), 121.78 (d, 1C, C$_1$, J$_{C1P}$=9.00 Hz), 127.52 (s, 1C, C$_4$, J$_{C4P}$=coupling not observed), 128.45 (s, 2C, C$_p$, J$_{CpP}$=1.73 Hz), 128.43 (d, 4C, C$_m$, J$_{CmP}$=8.44 Hz), 133.05 (d, 4C, C$_o$, J$_{CoP}$=13.92 Hz), 139.11 (d, 2C, C$_i$, J$_{CiP}$=9.76 Hz), 145.67 (d, 1C, C$_2$, J$_{C2P}$=32.55 Hz), 146.99 (d, 1C, C$_3$, J$_{C3P}$=14.09 Hz).
IR (KBr): ν (cm$^{-1}$)=3060 S, 3040 S, 2970 SS, 2940 SS, 2900 SS, 2860 S, 2820 S, 1620 S, 1580 m, 1520 w, 1470 S, 1430 SS, 1375 m, 1360 S, 1260 m, 1200 w, 1170 w, 1090 S, 1020 S, 970 SS, 810 m, 760 5, 730 SS, 690 SS.

Example B5

Perillic phosphine (Z)-C$_3$H$_5$(C$_6$H$_7$)[C$_2$H$_2$]PPh$_2$

The general procedure was followed, using 5 g of dimethyldiphenylphosphonium iodide A1 (14.61 mmol) and 2.4 ml (14.61 mmol) of (S)-(−)-perillaldehyde. The two isomers are separated on an alumina column with a hexane/dichloromethane eluent mixture (95/5).
The yield of the reaction is 70% (E/Z=48/52). The analyses on the product are given below.
Identification

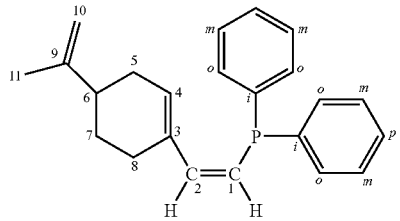 [SMILES: C=C(C)C1CC=C(/C=C\P(c2ccccc2)c2ccccc2)CC1]

Empirical formula: C$_{23}$H$_{25}$P.
Molecular weight: 332.20.
Melting point: 76° C. (hexane/dichloromethane).
$^{31}$P{$^1$H} NMR (CDCl$_3$): δ=−25.10 (s, 1P).
$^1$H NMR (CDCl$_3$): δ=1.73 (s, 3H, CH$_3$), 1.85 (m, 1H, CH), 2.07 (d, 2H, CH$_2$), 2.31 (m, 2H, CH$_2$), 2.57 (m, 2H, CH$_2$), 4.72 (m, 2H, CH$_2$), 5.87 (m, 1H, H$_4$), 6.06 (dd, 1H, J$_{H1H2}$=12.75 Hz, J$_{H1P}$=2.77 Hz), 6.80 (q, 1H, H$_2$, J$_{H2P}$=25.01 Hz), 7.33-7.47 (m, 10H, 2Ph).
$^{13}$C{$^1$H} NMR (CDCl$_3$): δ=20.86 (s, 1C, C$_H$), 27.66 (d, 1C, C$_7$, J$_{C7P}$=2.214 Hz), 29.23 (d, 1C, C$_8$, J$_{C8P}$=14.96 Hz), 31.46 (s, 1C, C$_5$), 40.53 (s, 1C, C$_6$), 108.86 (s, 1C, C$_{10}$), 125.5 (d, 1C, C$_1$, J$_{C1P}$=16.05 Hz), 128.30 (d, 2C, C$_p$, J$_{CpP}$=1.71 Hz), 128.52 (d, 4C, C$_m$, J$_{CmP}$=5.88 Hz), 132.47 (d, 4C, C$_o$, J$_{CoP}$=5.83 Hz), 132.92 (d, 1C, C$_4$, J$_{C4P}$=3.92 Hz), 136.52 (d, 1C, C$_3$, J$_{C3P}$=0.85 Hz), 140.54 (d, 2C, C$_i$, J$_{CiP}$=13.08 Hz), 146.67 (d, 1C, C$_2$, J$_{C2P}$=18.87 Hz), 149.58 (s, 1C, C$_9$).
IR (KBr): ν(cm$^{-1}$)=3060 S, 3040 S, 2960 S, 1680 m, 1555 m, 1475 m, 1430 SS, 1370 w, 1090 w, 1020 m, 970 w, 890 SS, 730 SS, 690 SS.

Example B6

Perillic phosphine (E)-C$_3$H$_5$(C$_6$H$_7$)[C$_2$H$_2$]PPh$_2$

Identification

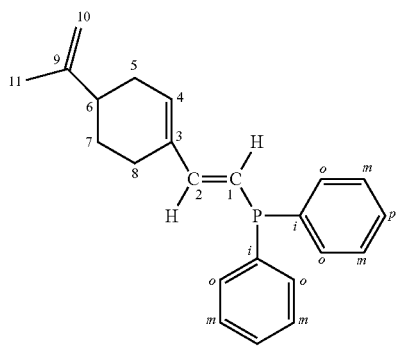 [SMILES: C=C(C)C1CC=C(/C=C/P(c2ccccc2)c2ccccc2)CC1]

Empirical formula: C$_{23}$H$_{25}$P.
Molecular weight: 332.20.
$^{31}$P{$^1$H} NMR (CDCl$_3$): δ=−12.96 (s, 19).
$^1$H NMR (CDCl$_3$): δ=1.78 (s, 3H, CH$_3$), 2.08 (m, 1H, CH), 2.38 (m, 6H, 3CH$_2$), 4.78 (m, 2H, CH$_2$), 5.88 (m, 1H, H$_4$), 6.25 (dd, 1H, H$_1$, J$_{H1P}$=6.16 Hz), 6.80 (t, 1H, Hz, J$_{H2H1}$=16.84 Hz), 7.26-7.47 (m, 10H, 2Ph).
$^{13}$C{$^1$H} NMR (CDCl$_3$): δ=21.61 (s, 1C, C$_{11}$), 24.93 (d, 1C, C$_7$, J$_{C7P}$=2.214 Hz), 26.38 (s, 1C, C$_8$, J$_{C8P}$=coupling not observed), 31.44 (s, 1C, C$_5$), 41.07 (s, 1C, C$_6$), 108.93 (s, 1C, C$_{10}$), 122.25 (d, 1C, C$_4$, J$_{C4P}$=8.75 Hz), 128.43 (d, 4C, C$_m$, J$_{CmP}$=2.76 Hz), 132.66 (s, 2C, C$_p$, J$_{CpP}$=coupling not observed), 132.91 (d, 4C, C$_o$, J$_{CoP}$=18.87 Hz), 135.79 (d, 1C, C$_3$, J$_{C3P}$=14.04 Hz), 138.99 (d, 2C, C$_i$, J$_{CiP}$=9.51 Hz), 147.58 (d, 1C, C$_1$, J$_{C1P}$=32.35 Hz), 149.43 (s, 1C, C$_9$), 150.58 (s, 1C, C$_2$, J$_{C2P}$=coupling not observed).
IR (KBr): ν (cm$^{-1}$)=3060 m, 3040 m, 2920 S, 1680 SS, 1660 S, 1580 w, 1560 w, 1470 w, 1445 w, 1430 SS, 1370 m, 1255 w, 1160 w, 1090 w, 1025 w, 970 S, 730 S, 690 SS.

Examples C

Preparations of cyclovinyl phosphine/-copper complexes

A Schlenk tube which beforehand has undergone three cycles of pump vacuum evacuation/baking/cooling/-nitrogen purging, is charged in succession with a cyclovinyl phosphine and a copper salt (in solid form). The reactor is purged under vacuum and then filled again with nitrogen. The solvent (acetonitrile) and then the copper salt (in liquid form) are subsequently added using syringes. The reactor is stirred at ambient temperature for half an hour.

Example C1

Dimeric 2((Z)vinylpyridine phosphine)/2CuI complex

The general procedure was followed, using 304 mg (1.047 mmol) of pyridine phosphine B1, 200 mg (1.047 mmol) of copper salt CuI, and 10 ml of acetonitrile. The orange precipitate formed is filtered off and then recrystallized from acetonitrile.

Yield: 480 mg (96%).

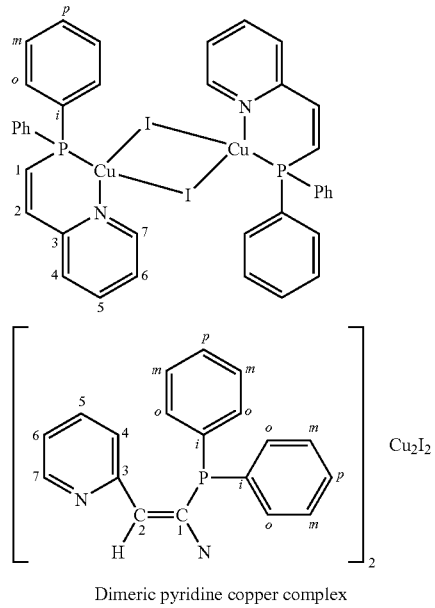

Dimeric pyridine copper complex

Empirical formula: $C_{38}H_{32}Cu_2I_2N_2P_2$.
Molecular weight: 958.82.
Melting point: 181-183° C. (acetonitrile).
$^{31}P\{^1H\}$ NMR (CDCl$_3$): δ=−32.77 (s, 1P).
$^1$H NMR (CDCl$_3$): δ=6.676 (dd, 1H, H$_1$, $J_{H1H2}$=13.0 Hz, $J_{H1P}$=2.5 Hz), 7.128 (ddd, 1H, H$_6$, $J_{H6H7}$=5.3 Hz, $J_{H6P}$=0.8 Hz), 7.181 (dd, 1H, H$_2$, $J_{H2P}$=30.8 Hz), 7.248 (m, 1H, H$_4$, $J_{H4H5}$=7.7 Hz, $J_{H4H6}$1.4 Hz, $J_{H4H7}$=1.8 Hz), 7.32-7.61 (m, 20H, 2Ph), 7.720 (td, 1H, H$_5$, $J_{H5H6}$=7.7 Hz, $J_{H5H7}$=1.8 Hz), 9.359 (broad d, 1H, H$_7$, $J_{H7P}$=1.9 Hz).
$^{13}C\{^1H\}$ NMR (CDCl$_3$): δ=124.08 (d, 1C, C$_6$, $J_{C6P}$=2.7 Hz), 128.57 (d, 1C, C$_m$, $J_{CmP}$=9.3), 128.67 (s, 1C, C$_p$, $J_{CpP}$=coupling not observed), 129.39 (d, 1C, C$_1$, $J_{C1P}$=19.6 Hz), 129.55 (d, 1C, C$_4$, $J_{C4P}$=1.6 Hz), 133.11 (d, 1C, C$_o$, $J_{CoP}$=15.0 Hz), 134.42 (d, 1C, C$_i$, $J_{CiP}$=28.7 Hz), 137.63 (s, 1C, C$_5$, $J_{C5P}$=coupling not observed), 141.79 (d, 1C, C$_2$, $J_{C2P}$=9.0 Hz), 152.28 (d, 1C, C$_3$, $J_{C3P}$=0.8 Hz), 154.05 ppm (d, 1C, C$_7$, $J_{C7P}$=1.8 Hz).
FAB-MS (positive mode): m/z=832 [(Ph$_2$PCHCHC$_5$H$_4$N)$_2$Cu$_2$I]$^+$, 543 [(Ph$_2$PCHCHC$_5$H$_4$N)$_1$Cu$_2$I]$^+$.
IR (KBr): ν (cm$^{-1}$)=3046 m, 1585 S, 1558 m, 1478 S, 1431 S, 1384 S, 1155 m, 1097 S, 1009 m, 998 w, 846 m, 805 SS, 749 S, 727 S, 695 SS, 649 m.

Example C2

Dimeric 2((Z)vinylpyridine phosphine)/1CuI complex

The general procedure is followed, using 100 mg (0.346 mmol) of pyridine phosphine B1, 33 mg (0.173 mmol) of copper salt CuI, and 5 ml of acetonitrile. After treatment, an orange-colored precipitate is obtained (copper complex 7).
Yield: T.F =100%.
Empirical formula: C38H32Cu2IN2P2.
Molecular weight: 831.2.
Melting point: 95-97° C. (acetonitrile).
31P{1H} NMR (CDCl3): δ=−24.34 (s, 1P) ppm.
1H NMR (CDCl3): δ=6.574 (dd, 1H, H1, JH1H2=13.0 Hz, JH1P=18.7 Hz), 7.128 (ddd, 1H, H6, JH6H7=5.3 Hz, JH6P=0.8 Hz), 7.630 (dd, 1H, H2, JH2P=39.1 Hz), 7.248 (m, 1H, H4, JH4H5=7.7 Hz, JH4H6=1.4 Hz, JH4H7=1.8 Hz), 7.32-7.61 (m, 20H, 2Ph), 7.720 (td, 1H, H5, JH5H6=7.7 Hz, JH5H7=1.8 Hz), 9.359 (broad d, 1H, H7, JH7P=1.9 Hz) ppm.
13C{1H} NMR (CDCl3): δ=124.08 (d, 1C, C6, JC6P=2.7 Hz), 128.29 (d, 1C, Cm, JCmP=6.7), 128.13 (s, 1C, Cp, JCpP=a), 129.39 (d, 1C, C1, JC1P=19.6 Hz), 129.55 (d, 1C, C4, JC4P=1.6 Hz), 132.77 (d, 1C, Co, JCoP=19.4 Hz), 135.39 (d, 1C, Ci, JCiP=21.0 Hz), 137.63 (s, 1C, C5, JC5P=a), 141.79 (d, 1C, C2, JC2P=9.0 Hz), 152.28 (d, 1C, C3, JC3P=0.8 Hz), 154.05 ppm (d, 1C, C7, JC7P=1.8 Hz).
FAB-MS (positive mode): m/z=642 [(Ph2PCHCHC5H4N)2Cu]+, 352 [(Ph2PCHCHC5H4N)Cu]+TOF-MS/ES+: m/z=641.15 [(Ph2PCHCHC5H4N)2Cu]+, 352.02 [(Ph2PCHCHC5H4N)Cu]+.
IR (KBr): ν (cm−1)=3045 m, 1582 S, 1556 m, 1478 S, 1432 SS, 1384 m, 1307 m, 1153 m, 1096 S, 1025 m, 997 m, 846 m, 803 SS, 744 S, 728 m, 695 SS, 651 m.

Example C3

(E)vinylpyridine phosphine/CuI complex

The above procedure is repeated, using pyridine phosphine B2.
Yield: 100%.
Melting point: 109-110° C. (acetonitrile).
$^{31}P\{^1H\}$ NMR (CDCl$_3$): δ=−15.00 (ΔW$_{1/2}$=187 Hz) (s, 1P).
$^1$H NMR (CDCl$_3$): δ=7.138 (ddd, 1H, H$_6$, $J_{H6H7}$=4.7 Hz), 7.146 (ddd, 1H, H$_4$, $J_{H4H5}$=7.7 Hz, $J_{H4H6}$=1.2 Hz, $J_{H4H7}$=0.9 Hz), 7.176 (broad dd, 1H, H$_2$, $J_{H2H1}$=16.5 Hz, $J_{H2P}$=12.8 Hz), 7.204-7.597 (m, 10H, 2Ph), 7.422 (broad dd, 1H, H$_1$, $J_{H1P}$=14.5 Hz), 7.537 (td, 1H, H$_5$, $J_{H5H6}$=7.7 Hz, $J_{H5H7}$=1.8 Hz), 8.520 (ddd, 1H, H$_7$).
$^{13}C\{^1H\}$ NMR (CDCl$_3$): δ=123.01 (s, 1C, C$_4$, $J_{C4P}$=coupling not observed), 123.27 (s, 1C, C$_6$, $J_{C6P}$=coupling not observed), 126.96 (d, 1C, C$_1$, $J_{C1P}$=26.0 Hz), 128.51 (d, 1C, C$_m$, $J_{CmP}$=8.7), 129.64 (s, 1C, C$_p$, $J_{CpP}$=coupling not observed), 133.00 (d, 1C, C$_i$, $J_{CiP}$=30.2 Hz), 133.75 (d, 1C, C$_o$, $J_{CoP}$=13.5 Hz), 136.48 (s, 1C, C$_5$, $J_{C5P}$=coupling not observed), 144.22 (d, 1C, C$_2$, $J_{C2P}$=14.1 Hz), 149.52 ppm (s, 1C, C$_7$, $J_{C7P}$=coupling not observed), 154.25 (d, 1C, C$_3$, $J_{C3P}$=15.0 Hz).
IR (KBr): ν (cm$^{-1}$)=3047 m, 2964 m, 1579 S, 1558 m, 1466 S, 1432 SS, 1384 S, 1308 w, 1261 S, 1178 w, 1148 m, 1093 S, 1025 m, 975 m, 856 m, 802 S, 741 SS, 693 SS, 630 w.

Example C4

(E)vinylpyridine phosphine/CuI complex

The general procedure was followed, using 100 mg (0.346 mmol) of pyridine phosphine B2, 66 mg (0.346 mmol) of copper salt CuI, and 5 ml of acetonitrile. After treatment, a yellow-colored precipitate is obtained (copper complex 9).
Yield: T.F=100%.
Melting point: 195-197° C. (acetonitrile).
31P{1H} NMR (CDCl3): δ=−22.97 (ΔW1/2=1550 Hz) (s, 1P) ppm.

1H NMR (CDCl3): δ=7.141 (ddd, 1H, H6, $J_{H6H7}$=4.9 Hz), 7.180 (ddd, 1H, H4, JH4H5=7.8 Hz, JH4H6=1.2 Hz, JH4H7=0.8 Hz), 7.410 (broad d, 1H, H2, JH2H1=16.7 Hz, JH2P=a), 7.266-7.692 (m, 10H, 2Ph), 7.488 (broad dd, 1H, H1, JH1P=11.8 Hz), 7.515 (td, 1H, H5, JH5H6 =7.5 Hz, JH5H7 =1.8 Hz), 8.583 (ddd, 1H, H7) ppm. 13C{1H} NMR (CDCl3): δ=123.14 (s, 1C, C4, JC4P=a), 123.37 (s, 1C, C6, JC6P=a), 127.05 (d, 1C, C1, JC1P=29.1 Hz), 128.51 (d, 1C, Cm, JCmP=9.4), 129.64 (s, 1C, Cp, JCpP=a), 132.96 (d, 1C, Ci, JCiP=32.0 Hz), 133.82 (d, 1C, Co, JCoP=13.5 Hz), 136.72 (s, 1C, C5, JC5P=a), 144.94 (d, 1C, C2, JC2P=15.1 Hz), 149.75 ppm (s, 1C, C7 JC7P=a), 154.37 (d, 1C, C3, JC3P=16.2 Hz).

IR (KBr): ν (cm−1)=3049 m, 3000 m, 1579 S, 1560 m, 1480 m, 1466 m, 1432 S, 1384 m, 1308 w, 1261 m, 1178 w, 1150 w, 1096 S, 1025 m, 970 m, 857 m, 804 S, 763 S, 739 SS, 692 SS, 631 w.

Examples D

Arylation reactions—General procedure

A 35 ml Schlenk tube, which beforehand had undergone three cycles of pump vacuum evacuation/baking/cooling/-nitrogen purging, is charged in succession with a copper salt, a cyclovinyl phosphine (ligand), a nucleophile, and optionally a base.

The arylating agent and then the solvent (acetonitrile) are then added using syringes. The reactor is taken to the desired temperature and stirred at that temperature for the time indicated in each of the examples below.

Example D1

Arylation of pyrazole

From Iodobenzene

The general procedure (acetonitrile, 82° C., 3 hours) was followed, using 9.52 mg (0.05 mmol) of copper iodide CuI, 28.9 mg (0.1 mmol) of vinylpyridine phosphine B1, 68 mg (0.75 mmol) of pyrazole, 326 mg (1 mmol) of cesium carbonate $Cs_2CO_3$, 56 μl (0.5 mmol) of iodobenzene, and 500 μl of acetonitrile.

The oil obtained after treatment was purified by chromatography on a silica column (eluent: dichloromethane/hexane 50/50).

Yield: 70 mg of colorless oil (98%).

From Bromobenzene

The general procedure (acetonitrile, 82° C., 4 hours) was followed, using 9.52 mg (0.05 mmol) of copper iodide CuI, 28.9 mg (0.1 mmol) of vinylpyridine phosphine Bi, 68 mg (0.75 mmol) of pyrazole, 326 mg (1 mmol) of cesium carbonate $Cs_2CO_3$, 53 μl (0.5 mmol) of bromobenzene, and 500 μl of acetonitrile.

The oil obtained after treatment was purified by chromatography on a silica column (eluent: dichloromethane/hexane 50/50).

Yield: 71 mg of colorless oil (99%).

Identification

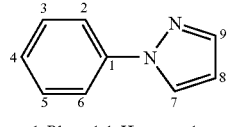

1-Phenyl-1-H-pyrazole $^1$H NMR (CDCl$_3$): δ 6 7.95-7.96 (dd, 1H, H$_7$); 7.71-7.75 (m, 3H, H$_{2,6,9}$); 7.47-7.50 (m, 2H, H$_{3,5}$); 7.28-7.34 (m, 1H, H$_4$); 6.49-6.50 (dd, 1H, H$_8$).

$^{13}$C NMR (CDCl$_3$): δ 141.09 (C$_9$); 140.22 (C$_1$); 129.45 (C$_{3,5}$), 126.75 (C$_7$); 126.46 (C$_4$); 119.23 (C$_{2,6}$); 107.61 (C$_8$).

IR (KBr): ν (cm$^{-1}$)=3142; 3050; 2924; 1600; 1520; 1500; 1393; 1332; 1198; 1120; 1046; 936; 914; 755; 689; 654; 610; 515.

GC/MS: rt=14.53 min, M/Z=144.

HRMS: 145.0766 (M+H). Theory: 145.0766.

Example D2

Arylation of 3,5-dimethylphenol

From Iodobenzene

The general procedure (acetonitrile, 82° C., 3 hours) was followed, using 9.52 mg (0.05 mmol) of copper iodide CuI, 28.9 mg (0.1 mmol) of vinylpyridine phosphine B1, 91.62 mg (0.75 mmol) of 3,5-dimethylphenol, 212 mg (1 mmol) of potassium phosphonate $K_3PO_4$, 56 μl (0.5 mmol) of iodobenzene, and 500 μl of acetonitrile.

The oil obtained after treatment was purified by chromatography on a silica column (eluent: hexane).

Yield: 95 mg of colorless oil (96%).

From Bromobenzene

The general procedure (acetonitrile, 82° C., 4 hours) was followed, using 9.52 mg (0.05 mmol) of copper iodide CuI, 28.9 mg (0.1 mmol) of vinylpyridine phosphine B1, 91.62 mg (0.75 mmol) of 3,5-dimethylphenol, 212 mg (1 mmol) of potassium phosphonate $K_3PO_4$, 53 μl (0.5 mmol) of bromobenzene, and 500 μl of acetonitrile.

The oil obtained after treatment was purified by chromatography on a silica column (eluent: hexane).

Yield: 97 mg of colorless oil (98%).

Identification

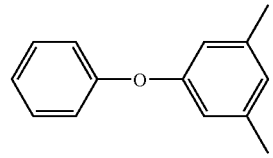

3,5-dimethyldiphenyl ether $^1$H NMR (CDCl$_3$): δ=7.28-7.42 (m, 2H); 7.12-7.17 (m, 1H); 7.03-7.14 (m, 2H); 6.79 (m, 1H); 6.69 (m, 2H); 2.33 (s, 6H, CH$_3$).

$^{13}$C NMR (CDCl$_3$): δ=157.50 (Cq); 157.22 (Cq); 139.61 (2 Cq); 129.70 (2CH); 125.04 (CH); 123.02 (CH); 118.89 (2 CH); 116.67 (2 CH); 21.35 (2 CH$_3$).

GC/MS: rt=18.24 min, M/Z=198.

Rf: 0.22 (eluent: hexane).

The invention claimed is:

1. A method for the preparation of a complex comprising contacting metallic copper or copper derivative, with a cyclovinyl phosphine of formula (I):

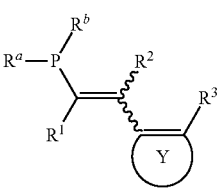

(1)

in which formula:

$R^a$ and $R^b$, which are identical or different, each represent a radical independently selected from alkyl, aryl, heteroaryl, monoalkylamino, dialkylamino, alkoxy, aryloxy, heteroaryloxy, or a radical —CR$^1$=CHR$^2$—CHR$^3$=CR$^4$R$^5$;

$R^1$ is hydrogen, or alkyl;

$R^2$ and $R^3$, which are identical or different, are selected independently from the group consisting of hydrogen, a hydrocarbon radical, an aryl radical, and a heteroaryl radical; and the ring Y represents a mono-, bi- or tri-cyclic nucleus comprising:
- a total of 5 to 20 members;
- optionally one or more heteroatoms selected from nitrogen, oxygen, sulfur, and phosphorus; and
- optionally one or more other intracyclic double bonds;
- said ring Y is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —$NO_2$, —$NH_2$, —CN, and $PR^aR^b$, where $R^a$ and $R^b$ are as defined above.

2. The method as claimed in claim 1, wherein the ring Y present in the phosphine of formula (I) is a mono-, bi- or tri-cyclic, aromatic or nonaromatic nucleus which optionally carries one or more heteroatoms selected from nitrogen, oxygen, sulfur, and phosphorus.

3. The method as claimed in claim 1, wherein the ring Y present in the phosphine of formula (I) is selected from cyclopentene, cyclopentadiene, pyrroles, imidazoles, pyrrolines, imidazolines, pyrazolines, furan, dihydrofuran, thiophene, dihydrothiophene, isoxazoles, thiazoles, and isothiazoles, and also their dihydrogenated analogs, benzene, cyclohexadienes, cyclohexene, pyridine and its di- and tetra-hydrogenated analogs, pyrazines, pyrimidines, and pyridazines and their di- and tetra-hydrogenated analogs, pyrans and dihydropyrans, triazine and its di- and tetra-hydrogenated analogs, dithiazine, cycloheptene, cycloheptadienes, azepines and their partially hydrogenated analog, cyclooctene, cyclooctadienes, cyclooctatriene, azocines, pentalene, indane, indenes, bornenes, norbornenes, naphthalene, azulene, heptalene, cyclopentacyclo-octene, benzocycloheptenes, benzocyclooctene, indolizinc, indole, isoindole, quinazolines, quinoline, isoquinoline, phthalazine, naphthyridine, quinoxaline, cinnoline, chromans, isochromans, chromenes and isochromenes, indolines and isoindolincs, indacenes, acenaphthylenes, fluorene, phenalene, phenanthrene, anthracene, thianthrene, xanthene, phenoxathiine, carbazoles, carboline, phenanthridine, acridine, perimidine, phenanthroline, phenazine, phenothiazine, phenoxazine, and their partially hydrogenated analogs.

4. The method as claimed in claim 1, wherein the compound of formula (I) possesses the following characteristics, taken in isolation or in combination of two or more thereof:

$R^a$ and $R^b$, which are identical or different, each represent a radical independently selected from the group consisting of alkyl, aryl, and heteroaryl;

$R^1$ represents hydrogen or an alkyl selected from the group consisting of, methyl, ethyl and propyl;

$R^2$ and $R^3$, which are identical or different, are selected independently from the group consisting of hydrogen, an alkyl radical, an aryl radical, and a heteroaryl radical; and Y represents a mono-, bi- or tri-cyclic nucleus, and optionally 1, 2 or 3 heteroatoms selected from the group consisting of nitrogen, oxygen, and sulfur.

5. The method as claimed in claim 1, wherein the compound of formula (I) possesses the following characteristics:

$R^a$ and $R^b$, which are identical or different, each represent a radical independently selected from the group consisting of aryl and heteroaryl;

$R^1$, $R^2$, and $R^3$, which are identical or different, are selected independently from the group consisting of hydrogen and an alkyl radical; and Y represents a monocyclic nucleus and optionally 1, 2 or 3 heteroatoms.

6. A compound which is a complex of copper with at least one cyclovinyl phosphine of formula (I):

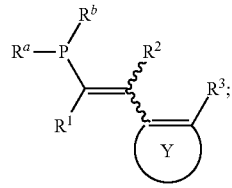

(1)

in which:

$R^a$ and $R^b$, which are identical or different, each represent a radical independently selected from the group consisting of alkyl, aryl, heteroaryl, monoalkylamino, dialkylamino, alkoxy, aryloxy, heteroaryloxy, or a radical —$CR^1$=$CHR^2$—$CHR^3$=$CR^4R^5$;

$R^1$ is hydrogen, or alkyl;

$R^2$ and $R^3$, which are identical or different, are selected independently from hydrogen, a hydrocarbon radical, an aryl radical, and a heteroaryl radical; and the ring Y represents a mono-, bi- or tri-cyclic nucleus comprising:
- a total of 5 to 20 members;
- optionally one or more heteroatoms selected from nitrogen, oxygen, sulfur, and phosphorus; and
- optionally one or more other intracyclic double bonds;
- said ring Y is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —$NO_2$, —$NH_2$, —CN, and $PR^aR^b$, where $R^a$ and $R^b$ are as defined above.

7. The compound as claimed in claim 6, wherein the complex is the dimeric pyridylvinyldiphenylphosphine/copper iodide complex $[C_5H_4N$—CH=CH—$PPh_2]_2Cu_2I_2$, where Ph represents the phenyl radical.

8. The compound as claimed in claim 6, wherein the complex is the monomeric pyridylvinyldiphenylphosphine/copper iodide complex [Py-CH=CH=$PPh_2]_2$CuI, where Ph represents the phenyl radical and Py represents pyridyl, in the form of the Z or E isomer, pure or as a mixture of said two isomers in any proportions.

9. A method of creating a carbon-carbon (C—C) bond or carbon-heteroatom (C—HE) bond by reacting a compound which carries a leaving group with a nucleophilic compound which carries a carbon atom or a heteroatom (HE) which can be capable of replacing the leaving group, thereby creating a C—C or C—HE bond, in which method the reaction is carried out in the presence of an effective amount of a catalyst system comprising at least one cyclovinyl phosphine/copper complex wherein the cyclovinyl phosphine has the formula (I):

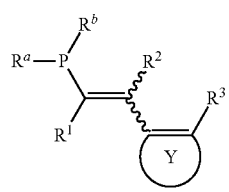

(1)

in which:

$R^a$ and $R^b$, which are identical or different, each represent a radical independently selected from the group consisting of alkyl, aryl, heteroaryl, monoalkylamino, dialkylamino, alkoxy, aryloxy, heteroaryloxy, or a radical —CR$^1$=CHR$^2$—CHR$^3$=CR$^4$R$^5$;

R$^1$ is selected from the group consisting of hydrogen, a hydrocarbon radical, and a heteroaryl radical;

R$^2$ and R$^3$, which are identical or different, are selected independently from hydrogen, a hydrocarbon radical, an aryl radical, and a heteroaryl radical; and the ring Y represents a mono-, bi- or tri-cyclic nucleus comprising:
  a total of 5 to 20 members;
  optionally one or more heteroatoms selected from nitrogen, oxygen, sulfur, and phosphorus; and
  optionally one or more other intracyclic double bonds;
  said ring Y is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —NO$_2$, —NH$_2$, —CN, and PR$^a$R$^b$, where R$^a$ and R$^b$ are as defined above.

10. The method as claimed in claim 9, wherein the cyclovinyl phosphine/copper complex is dimeric pyridylvinyldiphenylphosphine/copper iodide complex [C$_5$H$_4$N—CH=CH—PPh$_2$]$_2$Cu$_2$I$_2$, where Ph represents the phenyl radical or the monomeric pyridylvinyldiphenylphosphine/copper iodide complex [Py-CH=CH=PPh$_2$]$_2$CuI, where Ph represents the phenyl radical and Py represents pyridyl, in the form of the Z or E isomer, pure or as a mixture of said two isomers in any proportions.

11. The method as claimed in claim 10, wherein the compound which carries a leaving group is a compound comprising a double bond or a triple bond in a position to said leaving group, or an aromatic compound.

12. The method as claimed in claim 10, wherein the nucleophilic compound is an acyclic, cyclic or polycyclic organic hydrocarbon compound comprising at least one atom which carries a lone pair, which may or may not comprise a charge.

13. The method as claimed in claim 10, wherein the number of moles of the compound which carries the leaving group and the number of moles of the nucleophilic compound is between 0.1 and 2.0.

14. The method as claimed in claim 10, wherein the total amount of cyclovinyl phosphine/copper complex catalyst, expressed by the molar ratio between the number of moles of complex, expressed as copper, and the number of moles of compound which carries a leaving group, is between 0.001 and 0.5.

15. The method as claimed in claim 10, wherein a base is used whose pKa is between 4 and 30.

16. The method as claimed in claim 10, wherein a base is used which is selected from alkali metal or alkaline earth metal carbonates, hydrogen carbonates, phosphates or hydroxides, alkali metal hydrides, alkali metal alkoxides, and tertiary amines.

17. The method as claimed in claim 10, which is carried out in the presence of a polar organic solvent, preferably in the presence of an aprotic polar organic solvent.

18. The method as claimed in claim 10, wherein the nucleophilic compound and/or the compound which carries the leaving group is (are) used as reaction solvent(s).

19. The method as claimed in claim 10, wherein the cyclovinyl phosphine/copper complex is prepared in situ.

20. The method as claimed in claim 9, wherein R$^1$ is hydrogen or alkyl.

21. The method as claimed in claim 4, wherein R$^a$ and R$^b$, which arc identical or different, each represent a radical independently selected from the group consisting of:
  a) an alkyl selected from the group consisting of methyl, ethyl, propyl and butyl;
  b) an aryl selected from the group consisting of phenyl and naphthyl; and
  c) a heteroaryl selected from the group consisting of pyridyl and quinolyl.

22. The method as claimed in claim 4, wherein R$^a$ and R$^b$ are identical and each represent phenyl.

23. The method as claimed in claim 4, wherein R$^2$ and R$^3$ are selected from the group consisting of:
  a) hydrogen;
  b) an alkyl radical selected from the group consisting of methyl, ethyl and propyl,
  c) an aryl radical; and
  d) a heteroaryl radical.

24. The method as claimed in claim 4, wherein Y is a monocyclic nucleus comprising 5 or 6 members.

25. The method as claimed in claim 4, wherein Y is an aromatic nucleus which is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —NO$_2$, —NH$_2$, —CN, and PR$^a$R$^b$, where R$^a$ and R$^b$ are as defined in claim 4.

26. The method as claimed in claim 5, wherein where R$^a$ and R$^b$, which are identical or different, each represent a radical independently selected from the group consisting of:
  a) an aryl selected from the group consisting of phenyl and naphthyl,
  b) a heteroaryl selected from the group consisting of pyridyl and quinolyl.

27. The method as claimed in claim 5, wherein R$^a$ and R$^b$ are identical and each represent phenyl.

28. The method as claimed in claim 5, wherein R$^1$, R$^2$, and R$^3$, which are identical or different, ere selected independently from the group consisting of:
  a) hydrogen; and
  b) an alkyl radical selected from the group consisting of methyl, ethyl and propyl.

29. The method as claimed in claim 5, wherein Y is a monocyclic nucleus comprising 5 or 6 members.

30. The method as claimed in claim 5, wherein Y is an aromatic nucleus which is optionally substituted by one or more chemical species selected from alkyl-G-, alkenyl-G-, alkynyl-G-, aryl-G-, heteroaryl-G- (where G represents a bond, the oxygen atom or the sulfur atom), halogen, —NO$_2$, —NH$_2$, —CN, and PR$^a$R$^b$, where R$^a$ and R$^b$ are as defined in claim 5.

31. The method as claimed in claim 5, wherein Y is optionally a heteroatom selected from the group consisting of nitrogen, oxygen and sulfur.

32. The method as claimed in claim 12, wherein the nucleophilic compound is an acyclic, cyclic or polycyclic organic hydrocarbon compound comprising at least one atom selected from the group consisting of nitrogen, oxygen, sulfur, boron, phosphorus atom and a carbon atom which can donate its pair of electrons.

33. The method as claimed in claim 13, wherein the number of moles of the compound which carries the leaving group and the number of moles of the nucleophilic compound is between 0.5 and 1.5.

34. The method as claimed in claim 13, wherein the number of moles of the compound which carries the leaving group and the number of moles of the nucleophilic compound is between 0.8 and 1.2.

35. The method as claimed in claim 13, wherein the number of moles of the compound which carries the leaving group and die number of moles of the nucleophilic compound is between 0.9 and 1.1.

36. The method as claimed in claim 14, wherein the total amount of cyclovinyl phosphine/copper complex catalyst, expressed by the molar ratio between the number of moles of complex, expressed as copper, and the number of moles of compound which carries a leaving group is between 0.01 and 0.1.

37. The method as claimed in claim 17, wherein the polar organic solvent is an aprotic polar organic solvent.

38. The method as claimed claim 1, wherein $R^a$ and $R^b$ are identical.

* * * * *